(12) United States Patent
Greenberg

(10) Patent No.: US 6,897,019 B1
(45) Date of Patent: May 24, 2005

(54) METHODS FOR TREATING AND PREVENTING INSULIN RESISTANCE AND RELATED DISORDERS

(76) Inventor: Andrew S. Greenberg, 711 Washington St., Boston, MA (US) 02111

(*) Notice: Subject to any disclaimer, the term of this patent is extended or adjusted under 35 U.S.C. 154(b) by 253 days.

(21) Appl. No.: 09/690,647

(22) Filed: Oct. 17, 2000

Related U.S. Application Data

(63) Continuation-in-part of application No. PCT/US99/08364, filed on Apr. 16, 1999.
(60) Provisional application No. 60/082,741, filed on Apr. 23, 1998, and provisional application No. 60/082,152, filed on Apr. 17, 1998.

(51) Int. Cl.$^7$ .......................... C12Q 1/68; G01N 33/53; C07K 5/00; C07K 14/00; C07K 16/00

(52) U.S. Cl. .......................... 435/6; 435/7.1; 530/300; 530/350; 530/387.1; 536/23.1; 536/24.5

(58) Field of Search ............................. 514/44; 435/6, 435/375, 325, 366; 536/23.1, 24.5

(56) References Cited

U.S. PATENT DOCUMENTS

| | | | |
|---|---|---|---|
| 5,405,941 A | 4/1995 | Johnson | |
| 5,459,036 A | 10/1995 | Lechner et al. | |
| 5,534,426 A | 7/1996 | Karin et al. | |
| 5,593,884 A | 1/1997 | Karin et al. | |
| 5,595,904 A | 1/1997 | Boulton et al. | |
| 5,605,808 A | 2/1997 | Karin et al. | |
| 5,663,313 A | 9/1997 | Hawkins et al. | |
| 5,663,314 A | 9/1997 | Seger et al. | |
| 5,708,012 A | 1/1998 | Olefsky | |
| 5,712,265 A | 1/1998 | Cincotta et al. | |
| 5,712,283 A | 1/1998 | Kaan et al. | |
| 5,730,975 A | 3/1998 | Hotamisligil | |
| 5,804,399 A | 9/1998 | Karin et al. | |
| 5,837,244 A | 11/1998 | Karin et al. | |
| 5,859,051 A | 1/1999 | Adams et al. | |
| 5,994,513 A | 11/1999 | Karin et al. | |
| 6,001,584 A | 12/1999 | Karin et al. | |
| 6,110,948 A | * 8/2000 | Momose et al. | ............ 514/343 |
| 6,193,965 B1 | 2/2001 | Karin et al. | |
| 6,255,059 B1 | * 7/2001 | Klein et al. | ................. 435/731 |
| 6,342,595 B1 | 1/2002 | Karin et al. | |
| 6,514,745 B1 | 2/2003 | Karin et al. | |

FOREIGN PATENT DOCUMENTS

| | | |
|---|---|---|
| WO | WO 94/23039 | 10/1994 |
| WO | WO 95/21923 | 8/1995 |
| WO | WO 96/36642 | 11/1996 |
| WO | WO 97/02347 | 1/1997 |
| WO | WO 97/06245 | 2/1997 |

OTHER PUBLICATIONS

L G D Fryer et al., Selective modification of insulin action in adipose tissue by hyperthyroidism, Journal of Endocrinology (1997) 154 pp. 513–522.*

W. Michael Flanagan et al., Cellular penetration and antisense activity by a phenoxazine–substituted heptanucleotide, RESEARCH.*
Andrea D. Branch, A good antisense molecule is hard to find, TIBS 23—Feb. 1998, pp. 45–50.*
Ricote, M. et al. (1998), The Peroxisome Proliferator–Activated Receptor–γ is a Negative Regulator of Macrophage Activation, Nature 391:79.
Jiang, C. et al. (1998), PPAR–γ Agonists Inhibit Production of Monocyte Inflammatory Cytokines, Nature 391:82.
Shepard, P. et al. (1999), Glucose Transporters and Insulin Action, New Eng. J. of Med. 341(4):248.
Knopp, R. (1999), Drug Treatment of Lipid Disorders, New Eng. J. of Med. 341(7):498.
Suga, J. et al. (1997), Differential Activation of Mitoge–Activated Protein Kinase by Insulin and Epidermal Growth Factor in 3T3–L1 Adipocytes, Diabetes 46:735.
Hotamisligil, G. et al. (1994), Reduced Tyrosine Kinase Activity of the Insulin Receptor in Obesity–Diabetes, J. Clin. Invest. 94:1543.
Kim, S. et al. (1997), Insulin Regulation of Mitogen–Activated Protein Kinase Kinase (MEK), Mitogen–Activated Protein Kinase and Casoin Kinase in the Cell Nucleus: A Possible Role in the Regulation of the Gene Expression, Biochem J. 323:621.
Souza, S. et al. (1998), BRL 49653 Blocks the Lipolytic Actions of Tumor Necrosis Factor–α, Diabetes 47:691.
Souza, S. et al. (1997), Salicylic Acid Decreases the Ability of Tumor Necrosis Factor (TNF–α) to Increase Lipolysis in 313–L1 Adipocytes, FASEB J. 11(3):919.
Wang, C. et al. (1998), Effects of Cell–Permeable Ceramides and Tumor Necrosis Factor–α on Insulin Signaling and Glucose Uptake in 313–L1 Adipocytes, Diabetes 47:24.
Hu, E. et al. (1996), Inhibition of Adipogenesis Through MAP Kinase–Mediated Phosphorylationh of PPARγ, Science 274:2100.
Biomol Research News (1997), Antisense Reagents, 6(1).
Rizzo, M. et al. (1996), Arachidonic Acid Mediates Interleukin–1 and Tumor Necrosis Factor–α–Induced Activation of the c–jun Amino Terminal Kinases in Stromal Cells, Blood 88(10):3792.
Robertson, R.P. (1988), Eicosanoids as Pluripotential Modulators of Pancreatic Islet Function, Diabetes 37:367.

(Continued)

Primary Examiner—John L. LeGuyader
Assistant Examiner—J D Schultz

(57) ABSTRACT

The invention provides methods, therapeutics and kits for treating and preventing diseases or conditions associated with excessive lipolysis, in particular TNF-α induced lipolysis, and/or excessive free fatty acid levels. Exemplary conditions include insulin-resistance, diabetes, in particular NIDDM, obesity, glucose intolerance, hyperinsulinemia, polycystic ovary syndrome, and coronary artery disease. In a preferred embodiment, the method includes administering to a subject in need a pharmaceutically effective amount of an inhibitor of the JNK signal transduction pathway and/or an inhibitor of the MAPK/ERK signal transduction pathway.

4 Claims, 14 Drawing Sheets

OTHER PUBLICATIONS

Tebbey, P. et al. (1994), Arachidonic Acid Down–Regulates the Insulin–Dependent Glucose Transporter Gene (GLUT4) in 3T3–L1 Adipocytes by Inhibiting Transcription and Enhancing mRNA Turnover, *J. Bio. Chem.* 269(1):639.

Feinstein, R. et al. (1993), Tumor Necrosis Factor–α Suppresses Insulin–Induced Tyrosine Phosphorylation of Insulin Receptor and its Substrates, *J. Bio. Chem.* 268(35):26055.

Lehmann, J. et al. (1995), An Antidiabetic Thiazolidinedione is a High Affinity Ligend for Peroxisome Proliferator–Activated Receptor γ (PPARγ), *J. Bio. Chem.* 270(22):12953.

Ibrahimi, A. et al. (1994), Evidence for a Common Mechanism of Action for Fatty Acids and Thiazolidinedione Antidiabetic Agents on Gene Expression in Preadipose Cells, *Molecular Pharmacology* 46:1070.

Cobb, M.H. et al. (1995), How MAP Kinases are Regulated, *J. Bio. Chem.* 270(25):14843.

Liu, Z. et al. (1996), Dissection of TNF Receptor 1 Effector Functions: JNK Activation is Not Linked to Apoptosis While NF–κB Activation Prevents Cell Death, *Cell* 87:565.

Oakes, N. et al (1994), A New Antidiabetic Agent, BRL 49653, Reduces Lipid Availability and Improves Insulin Action and Glucoregulation in the Rat, *Diabetes* 43:203.

Vane, J.R. (1971), Inhibition of Prostaglandin Synthesis as a Mechanism of Action for Aspirin–Like Drugs, *Nature New Bio.* 231:232.

Kyriakis, J.M. et al. (1994), The Stress–Activated Protein Kinase Subfamily of c–Jun Kinases, *Nature* 369:156.

Vossler, M.R. et al. (1997), cAMP Activates MAP Kinase and Elk–1 Through a B–Raf– and Rap1–Dependent Pathway, *Cell* 89:73.

Feingold. K.R. et al. (1992), Stimulation of Lipolysis in Cultured Fat Cells by Tumor Necrosis Factor, Interleukin–1, and the Interferons is Blocked by Inhibition of Prostaglandin Synthesis, *Endo* 130(1):10.

Hotamisligil, G.S. et al. (1995), Increased Adipose Tissue Expression of Tumor Necrosis Factor–αin Human Obesity and Insulin Resistance, *J. Clin. Invest.* 95:2409.

Kern, P.A. et al (1995), The Expression of Tumor Necrosis Factor in Human Adipose Tissue, *J. Clin. Invest.* 95:2111.

Roden, M. et al. (1996), Mechanism of Free Fatty Acid–Induced Insulin Resistance in Humans, *J. Clin. Invest.* 97(12):2859.

Smith, U. (1994), Carbohydrates, Fat, and Insulin Action, *Am. J. Clin. Nutr.* 59:686S.

Nolan, J.J. et al. (1994), Improvement in Glucose Tolerance and Insulin Resistance in Obese Subjects Treated with Troglitazone, *New Eng. J. of Med.* 331(18):1188.

Beutler, B. (1995), TNF, Immunity and Inflammatory Disease: Lessons of the Past Decade, *J. Invest. Med.* 43(3):227.

Kroder, G. et al. (1996), Tumor Necrosis Factor–α–and Hyperglycemia–Induced Insulin Resistance, *J. Clin. Invest.* 97(6):1471.

Hardardottir, I. et al. (1992), Cytokines Stimulate Lipolysis and Decrease Lipoprotein Lipase Activity in Cultured Fat Cells by a Prostaglandin Independent Mechanism, *Biochem. And Biophys. Res. Comm.* 186(1): 237.

Zhang, C. et al. (1997), Mitogen–Activated Protein (MAP) Kinase Regulates Production of Tumor Necrosis Factor–α and Release of Arachidonic Acid in Mast Cells, *J. Bio. Chem.* 272(20):13397.

Lehmann. J.M. et al. (1997), Peroxisome Proliferator–Activated Receptors α and γ Are Activated by Indomethacin and Other Non–steroidal Anti–inflammatory Drugs, *J. Bio. Chem.* 272(6):3406.

Boden, G. (1997), Role of Fatty Acids in the Pathogenesis of Insulin Resistance and NIDDM, *Diabetes* 46:3.

Reaven, G.M. (1988), Role of Insulin Resistance in Human Disease, *Diabetes* 37:1595.

Hotamisligil, G.S. et al (1994), Tumor Necrosis Factor α: A Key Component of the Obesity–Diabetes Link, *Diabetes* 43:1271.

Dunaif, A. et al. (1996), The Insulin Sensitizing Agent Troglitazone Improves Metabolic and Reproductive Abnormalities in the Polycystic Ovary Syndrome, *J. Clin. Endocrinology and Metabolism* 81(9):3299.

Davis, R.J. (1994), MAPKs: New JNK Expands the Group, *TIBS* 19:470.

Long, S.D. (1996), Regulation of GLUT4 Gene Expression by Arachidonic Acid, *J. Bio. Chem.* 271(2):1138.

Tebbey, P.W. (1994), Arachidonic Acid Down–Regulates the Insulin–Dependent Glucose Transporter Gene (GLUT4) in 3T3–L1 Adipocytes by Inhibiting Transcription and Enhancing mRNA Turnover, *J. Bio. Chem.* 269(1):639.

Robertson, R.P. et al (1977), A Role for Prostaglandin E in Defective Insulin Secretion and Carbohydrate Intolerance in Diabetes Mellitus, *J. Clin. Invest.* 60:747.

Blumer, K.J. et al (1994), Diversity in Function and Regulation of MAP Kinase Pathways, *TIBS* 19:236.

Zhang, B. et al. (1996). Insulin– and Mitogen Activated Protein Kinase–Mediated Phosphorylation and Activation of Peroxisome Proliferator–Activated Receptor γ, *J. Bio. Chem.* 271(50):31771.

Szalkowski, D. et al. (1995), Antidiabetic Thiazolidinediones Block the Inhibitory Effect of Tumor Necrosis Factor–α on Differentiation, Insulin–Stimulated Glucose Uptake, and Gene Expression in 3T3–L1 Cells, *Endocrinology* 136(4):1474.

Fanger, G.R. et al. (1997), MEKKs, GCKs, MLKs, TAKs, and Tpls: Upstream Regulators of the c–Jun Amino–Terminal Kinases!, *Curr. Opin. Genetics and Development* 7:67.

Schwenger, P. et al (1996), Inhibition of Tumor Necrosis Factor–Induced p42/p44 Mitogen–Activated Protein Kinase Activation by Sodium Salicylate, *J. Bio. Chem.* 271(14):8089.

Schwenger, P. et al. (1997), Sodium Salicylate Induces Apoptosis Via p38 Mitogen–Activated Protein Kinase but Inhibits Tumor Necrosis Factor–Induced c–Jun N–Terminal Kinase/Stress–Activated Protein Kinase Activation, *Proc. Natl. Acad. Sci. USA* 94:2869.

Ehrmann, D.A. et al. (1997), Troglitazone Improves Defects in Insulin Action, Insulin Secretion, Ovarian Steroidogenesis, and Fibrinolysis in Women with Polycystic Ovary Syndrome, *J. Clin. Endocrinology and Metabolism* 82(7):2108.

Camp, H.S. et al. (1999), c–Jun N–Terminal Kinase Phosphorylates Peroxisome Proliferator–Activated Receptor–γ1 and Negatively Regulates Its Transcriptional Activity, *Endocrinology* 140(1):392.

Kyriakis, J.M. et al. (1996), Protein Kinase Cascades Activated by Stress and Inflammatory Cytokines, *BioEssays* 18(7):567.

Skolnik, E.Y. et al. (1996), Inhibition of Insulin Receptor Signaling by TNF: Potential Role in Obesity and Non-Insulin-Dependent Diabetes Mellitus, *Cytokine & Growth Factor Reviews* 7(2):161.

Lopes-Virella, M.F. et al. (1996), Cytokines, Modified Lipoproteins, and Arteriosclerosis in Diabetes, *Diabetes* 45(3):S40.

Pampfer, S. et al. (1997), Increased Synthesis of Tumor Necrosis Factor-α in Uterine Explants From Pregnant Diabetic Rats and in Primary Cultures of Uterine Cells in High Glucose, *Diabetes* 46:1214.

Haneda, M. et al (1997), Mitogen-Activated Protein Kinase Cascade is Activated in Glomeruli of Diabetic Rats and Glomerular Mesangial Cells Cultured Under High Glucose Conditions, *Diabetes* 46:847.

Argiles, J.M. et al. (1997), Journey from Cachexia to Obesity by TNF, *Faseb J.* 11 (10):743.

McMurray, R.W. (1996), Adhesion Molecules in Autoimmune Disease, *Semin Arthritis Rheum.* 25:215.

Ravussin, E. (1995), Metabolic Differences and the Development of Obesity, *Metabolism* 44(9):12.

Probert, L. et al. (1996), Dissection of the Pathologies Induced by Transmembrane and Wild-Type Tumor Necrosis Factor in Transgenic Mice, *J. Leukocyte Bio.* 59:518.

Bonni, A. et al. (1997), Regulation of Gliogenesis in the Central Nervous System by the JAK-STAT Signaling Pathway, *Science* 278:477.

Argiles, J.M. et al. (1994), Cytokines and Diabetes: The Final Step?, *Horm. Metab. Res.* 26:447.

Adams, M. et al. (1997), Transcriptional Activation by Perooxisome Proliferator-Activated Receptor γ is Inhibited by Phosphorylation at a Concensus Mitogen-Activated Protein Kinase Site, *J. Bio. Chem.* 272(8):5128.

Fromm, G.H. et al. (1993), A Clinical and Experimental Investigation of the Effects of Tizanidine in Trigeminal Neuralgia, *Pain* 53:265.

Samed, F. et al. (1997), The Fat Mouse: A Powerful Genetic Model to Study Elevated Plasminogen Activator Inhibitor 1 in Obesity/NIDDM, *Thromb. Haemost.* 78(1):652.

Flavell, R.A. et al. (1996), The Contribution of Insulitis to Diabetes Development in Tumor Necrosis Factor Transgenic Mice, *Curr. Top. Microbiol. Immunol.* 206:33.

Cunningham, J.M et al. (1994), Cytokines, Nitric Oxide and Insulin Secreting Cells, *Growth Regulation* 4:173.

Van De Merwe, T.J. et al. (1984), A Double-Blind Non-Crossover Placebo-Controlled Study Between Group Comparison of Trazodone and Amitriptyline on Cardiovascular Function in Major Depressive Disorder, *Psychopathology* 17(2):64.

Kellerer, M. et al. (1995), Pathogenesis of Insulin Resistance: Modulation of the Insulin Signal at Receptor Level, *Diabetes Res. And Clin. Prac.* 28:S173.

Di Tella, A.S. et al. (1986), Determination of Trazodone and Its Metabolite, m-CPP, in Serum and Urine by HPLC, *J. Analytical Toxicology* 10:233.

Hailer, H. et al. (1996), The Role of Hyperglycemia and Hyperinsulinemia in the Pathogenesis of Diabetic Angiopathy, *Clin. Nephrology* 46(4):246.

Sugumoto, H. (1996). Energy Substrate Metabolism During Stress, *Nippon Geka Gakkai Zasshi* 97(9):726.

PCT International Search Report, PCT/US99/08364.

Souza, S.C. et al. (1998), The P38 Map Kinase Inhibitor, SB 203580, Increases TNFα-Induced Lipolysis in 3T3-L1 Adipocytes, *Intl J. Obesity* 22:110.

Font de Mora, J. et al. (1997), Mitogen-Activated Protein Kinase Activation is not Necessary for, but Antagonizes, 3T3-L1 *Adipocytic Differentiation, Molecular and Cellular Bio.* 17(10):6068.

Schwenger, P. et al. (1998), Activation of p38 Mitogen-Activated Protein Kinase by Sodium Salicylate Leads to Inhibition of Tumor Necrosis Factor-Induced IκBα Phosphorylation and Degradation, *Molecular and Cellular Bio.* 18(1):78.

Vic-Mo. H. et al. (1978), Effects of Sodium Salicylate on Plasma Insulin Concentration and Fatty Acid Turnover in Dogs, *Acta. Physiol. Scand.* 103:113.

Schonhofer, P.S. et al. (1972), Effects of Sodium Salicylate and Acetylsalicylic Acid on the Lipolytic System of Fat Cells, *Biochem. Pharm.* 22:629.

Stone, Daniel B. et al. (1969), Effect of Sodium Saticylate on Induced Lipolysis in Isolated Fat Cells of the Rat, *Meatbolism* 18(7):620.

Kletzien, R. et al. (1995), Activation of a Novel Map Kinase by TNFα: Ramifications for Insulin Signal Transduction, *FASEB J.* XP002117006.

Foellmi-Adams, L.A. et al. (1995), Selective Attenuationof Insulin Activation of MAP Kinase by Tumor Necrosis Factor-α, *FASEB J.* XP002117007.

Sale, E.M. et al. (1995), Requirement of MAP Kinase for Differentiation of Fibroblasts to Adipocytes, for Insulin Activation of p90 S6 Kinase and for Insulin or Serum Stimulation of DNA Synthesis, *EMBO J.* 14(4):674.

Kliewer, S.A. et al. (1995). A prostaglandin J2 Metabolite Binds Peroxisome Proliferator—Activated Receptor γ and Promotes Adipocyte Differentiation, *Cell* 83:813.

Pearson, S.L et al.. (1996), The Thiazolidinedione Insulin Sensitiser, BRL 49653, Increases the Expression of PPAR-γ and aP2 in Adipose Tissue of High-Fat-Fed Rats, *Biochem. And Biophys. Res. Comm.* 229:752.

Souza, S.C. et al. (1998), the P38 MAP Kinase Inhibitor, SB 203580, Increases TNF-α-lnduced Lipolysis in 3T3-L1 Adipocytes, *Intl. J. Obesity* 22(3):P58.

Aguirre et al. The c-Jun NH(2)-terminal kinase promotes insulin resistance during association with insulin receptor substrate-1 and phosphorylatian of Ser(307). J Biol Chem. Mar 24, 2000;275(12):9047-54.

del Aguila et al. TNF-alpha impairs insulin signaling and Insulin stimulation of glucose uptake in C2C12 muscle cells. Am J Physiol. May 1999;276(5 Pt 1):E849-55.

Hotamisligil et al. Mechanisms of TNF-alpha-induced insulin resistance. Exp Clin Endocrinol Diabetes. 1999;107(2):119-25. Review.

La Marchand-Brustel, Y. Molecular mechanisms of insulin action in normal and insulin-resistant states. Exp Clin Endocrinol Diabetes. 1999;107(2):126-32. Review.

Liu et al. Tumor necrosis factor-alpha acutely inhibits insulin signaling in human adipocytes: implication of the p80 tumor necrosis factor receptor. Diabetes. Apr 1998;47(4):515-22.

Shin et al. An inhibitor of c-jun aminoterminal kinase (SP600125) represses c-Jun activation, DNA-binding and PMA-inducible 92-kDa type IV collagenase expression. Biochim Biophys Acta. May 8, 2002;1589(3):311-6.

Spiegelman et al. Regulation of adipocyte gene expression in differentiation and syndromes obesity/diabetes. J Biol Chem. Apr. 5, 1993;268(10):6823-6. Review.

Valverde et al. Tumor necrosis factor–alpha causes insulin receptor substrate–2–meduated insulin resistance and inhibits insulin–induced adipogenesis in fetal brown adipocytes. Endocrinology. Mar. 1998;139(3):1229–38.

Engelman el al. (2000). *Tumor Necrosis Factor α–Mediated Insulin Resistance. but Not Dedifferentiation is Abrogated by MEK1/2 Inhibitors in 3T3–L1 Adipocytes*. Molecular Endocrinology 14(10):1557.

Souza et al. (1998), *Overexpression of Perdipin A and B Blocks the Ability of Tumor Necrosis Factor α to Increase Lipolysis in 3T3–L1 Adipocytes*. J. Biol. Chem. 273(38):24665.

Edelstein Rosenbaum and Greenberg (1998). *The Short– and Long–Term Effects of Tumor Necrosis Factor–α and BRL 49653 on Peroxisome Proliferator–Activated Receptor (PPAR) Gene Expression and Other Adipocyte Genes*. Molecular Endocrinology 12(8):1150.

Greenberg et al.(1993), *Isolation of cDNAs for Perilipins A and B: Sequence and Expression of Lipid Droplet–Associated Proteins of Adipocytes*. Proc. Natl. acad. Sci. USA 90:12035.

Egan et al. (1992), *Mechanism of Hormone–Simulated Lipolysis in Adipocytes: Translocation of Hormone–Sensitive Lipase to the Lipid Storage Droplet*, Proc. Natl. Acad. Sci. USA 89:8537.

Camp et al. (1999), *c–Jun N–Terminal Kinase Phosphorylates Peroxisome Perliferator–Activated Receptor–Y and Negatively Regulates us Transcriptional Activity:* Endocrinology 140(1):392.

* cited by examiner

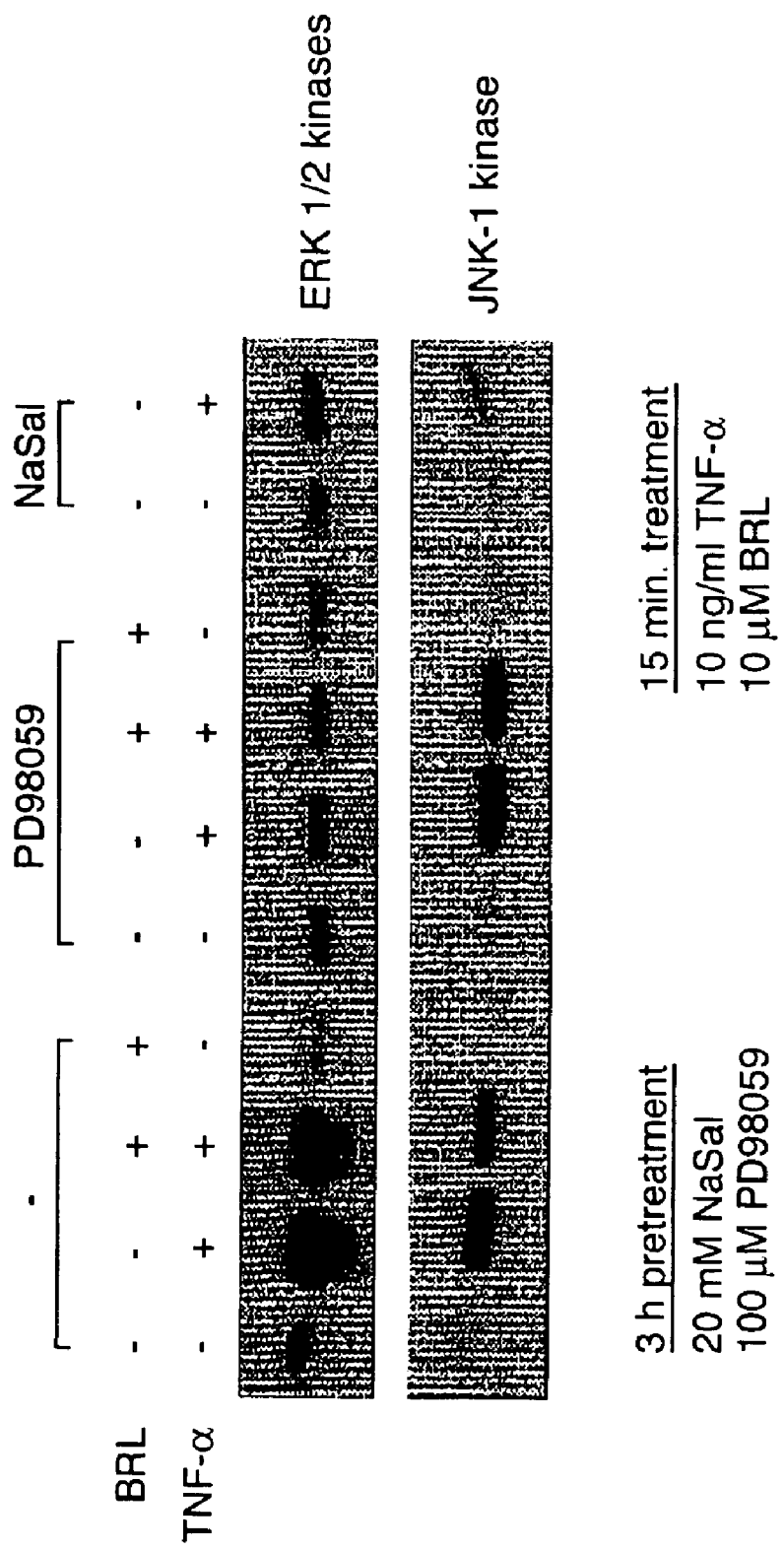

METHODS FOR TREATING AND PREVENTING INSULIN RESISTANCE AND RELATED DISORDERS

CROSS-REFERENCE TO RELATED APPLICATIONS

This application is a continuation-in part application of International Application No. PCT/US99/08364, filed Apr. 16, 1999, which claims the benefit of U.S. Provisional Application No. 60/082,152, filed Apr. 17, 1998 and U.S. Provisional Application No. 60/082,741, filed Apr. 23, 1998, the contents of which are specifically incorporated herein by reference.

STATEMENT OF RIGHTS

This invention was made with government support under 58-1950-9-001 awarded by the United States Department of Agriculture. The government has certain rights in the invention.

BACKGROUND OF THE INVENTION

Diabetes is one of the most prevalent chronic worldwide disease with significant personal and financial costs to patients and their families, as well as for society. Diabetes can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications, and diabetes and its complications are a leading cause of untimely death in the United States and in the Western world.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30–40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization.

Insulin deficiency is a common and serious pathologic condition in man. In insulin-dependent (IDDM or Type I) diabetes the pancreas produces little or no insulin, and insulin must be injected daily for the survival of the diabetic. In the second major type of diabetes, i.e., noninsulin-dependent (NIDDM or Type II) diabetes, the pancreas retains the ability to produce insulin and in fact may produce higher than normal amounts of insulin, but the amount of insulin is relatively insufficient, or less than fully effective, due to cellular resistance to insulin (Kosaka J., "The classification of disease based on the concept of Diabetes Mellitus", Nippon Rinsho 1990 extra number, Diabetes Mellitus, Nippon Rinsho Press, Osaka 1990, p. 161–168).

The number of patients with NIDDM is large and it is said that, e.g., in Japan, more than 90% of patients who suffer from Diabetes show NIDDM. This corresponds to about two million individuals in Japan only who have NIDDM.

In most NIDDM subjects, the fundamental defects to which the abnormalities can be traced are (1) a reduced entry of glucose into various "peripheral" tissues and (2) an increased liberation of glucose into the circulation from the liver. There is therefore an extracellular glucose excess and an intracellular glucose deficiency. There is also a decrease in the entry of amino acids into muscle and an increase in lipolysis. Hyperlipoproteinemia is also a complication of diabetes. The cumulative effect of these diabetes-associated abnormalities is severe blood vessel and nerve damage.

The importance of delaying or preventing NIDDM and other conditions associated with insulin resistance cannot be over-emphasized. Untreated NIDDM can result in mortality due to cardiovascular disease and in other diabetic complications including retinopathy, nephropathy, and peripheral neuropathy. Insulin resistance can also cause hypertension, obesity, aging, and coronary artery diseases.

In recent years, the significance of insulin resistance in NIDDM has been realized and this has created a desire for the development of a medication which exhibits an antidiabetic action without stimulating insulin secretion by reducing insulin resistance in the target tissues of the insulin. Thiazolidine derivatives such as troglitazone and pioglitazone have been developed as compounds which possess such an action (Japanese Patent Applications Laid-open No. 22636/1980, No. 51189/1985, and No. 157522/1994). Some other thiazolidine derivatives with a bicyclic lactam structure or a cyclic urethane structure which exhibit similar actions have been reported (WO 92/07838, WO 92/07839, and WO 92/07850). Other therapeutic agents for NIDDM include (1) stimulants for synthesis of insulin and regulators for secretion of it as agents for disorder of the secretion and the production, (2) agents for absorption of sugar, stimulants for the utilization, agents for glucose transporter, or suppressors of gluconeogenesis in liver as agents for regulation of hyperglycemia, (3) stimulants for the action of insulin or antiglycation agents as a suppressor for disorder caused by hyperglycemia, and other anti-complication agents, have been developed.

However, the effect of these compounds with insulin resistance-reducing activity on decreasing blood glucose or lipids is not sufficient Development of a compound which exhibits a stronger anti-diabetic action has been desired.

SUMMARY OF THE INVENTION

The invention provides methods and compositions for preventing or treating a disease or condition caused, or contributed to, by TNF-α-induced lipolysis and/or elevated levels of FFA and/or glycerol in an individual. In a preferred embodiment, the method comprises administering to an individual a pharmaceutically effective amount of a compound which modulates one or more MAP kinase pathways, to reduce lipolysis, to thereby prevent or treat the disease or condition in the individual. In an even more preferred embodiment, the compound is an inhibitor of ERK1, ERK2, and/or of the JNK pathways. Tthe inhibitor can be a direct inhibitor or an indirect inhibitor. For example, the inhibitor can decrease the protein level of ERK1/2 and/or JNK, or decrease expression of a gene encoding ERK1/2 and/or JNK. In certain embodiments the inhibitor interacts with an ERK1/2 and/or JNK gene and can be, e.g., an antisense molecule, a triplex molecule, or a ribozyme. Other MAP kinase inhibitors of the invention include those which inhibit ERK1/2 and/or phosphorylation.

The method of the invention can be used for treating or preventing insulin resistance in a subject, or any disease or condition associated therewith. Preferred diseases or conditions which can be treated according to the method of the invention also include diabetes, in particular NIDDM prediabetic conditions, polycystic ovary syndrome (PCOS), cardiovascular diseases, coronary artery diseases, and hyperinsulinemia.

Also within the scope of the invention is a method for determining whether a subject has or is likely to develop a disease or condition caused, or contributed to, by lipolysis, comprising determining the activity of a JNK in the individual, and wherein an abnormally high JNK activity indicates that the individual has or is likely to develop a disease or condition caused, or contributed to, by lipolysis. In an illustrative embodiment, determining the activity of a JNK comprises determining JNK protein level, wherein an abnormally high JNK protein level is an abnormally high JNK activity, or determining whether the JNK protein is a mutated JNK protein.

In yet another embodiment, the invention provides a drug screening method for identifying a compound which reduces TNF-α induced lipolysis. In a preferred embodiment, the screening method comprises (i) isolating a compound which is an ERK1/2 and/or JNK inhibitor; and (ii) contacting an adipocyte with the compound of step (i) and TNF-α and determining the level of lipolysis, wherein a lower level of lipolysis in the presence of the compound of step (i) relative to the level of lipolysis in the absence of the compound of step (i) indicates that the compound reduces lipolysis.

Other aspects of the invention are described below or will be apparent to those skilled in the art in light of the present disclosure.

BRIEF DESCRIPTION OF THE DRAWINGS

FIG. 6A represents a photograph of a Western blot depicting the activity ERK1/2 and JNK-1 kinases, as determined in a kinase assay, from cells that were preincubated for 3 hours with or without 20 nM sodium salicylate or 100 μM PD98059 and then treated for 15 minutes with or without BRL and TNF-α.

DETAILED DESCRIPTION OF THE INVENTION

1. General Overview

Figure 1A:
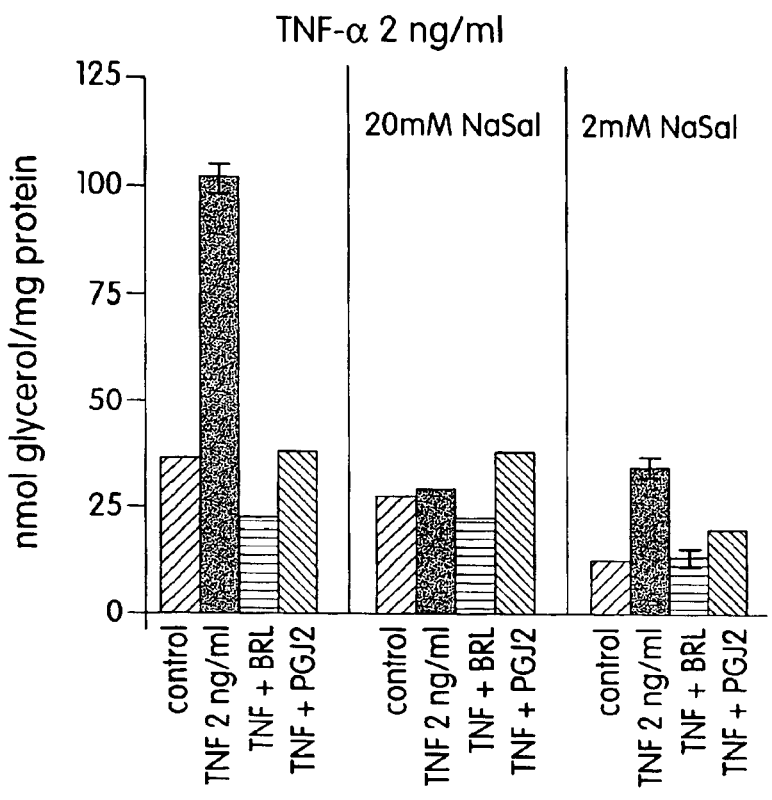
FIG. 1A shows the amount of glycerol produced from 3T3-L1 adipocytes incubated for 24 hours with or without sodium salicylate (NaSal), BRL, PGJ2 and 2 ng/ml TNF-α.
Figure 1B:
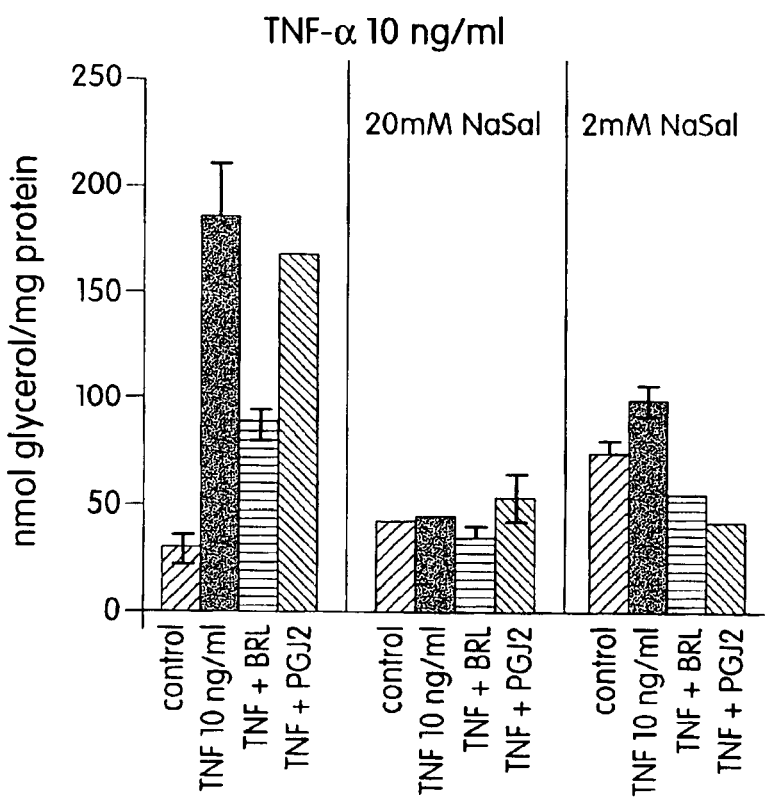
FIG. 1B shows the amount of glycerol produced from 3T3-L1 adipocytes incubated for 24 hours with or without sodium salicylate (NaSal), BRL, PGJ2 and 10 ng/ml (Panel B) TNF-α.

The invention pertains to methods for treating diseases or conditions caused by or contributed to by lipolysis, such as TNF-α induced lipolysis. Examples of such diseases or conditions include those arising from hyperlipidemia, hyperglycemia, obesity, impaired glucose tolerance (IGT), insulin resistant non-IGT (NGT), non-diagnostic glucose tolerance, insulin resistance, diabetic complications, fatty liver, polycystic ovary syndrome (PCOS) gestational diabetes mellitus (GDM), and hypertension. In a preferred embodiment of the invention, the disease is non-insulin dependent diabetes mellitus (NIDDM). In an even more preferred embodiment, the invention comprises administering to a subject an inhibitor of the inhibitor of the ERK/MAP kinase pathway and/or and an inhibitor of the JNK pathway. The method can further comprise administering to the subject a compound which stimulates the p38 pathway. In another embodiment, the method comprises administering to the subject an agonist of PPAR-γ, such as a prostaglandin derivative or BRL 49653.

The invention is based at least in part on the observation that TNF-α induced lipolysis, which has been implicated in various diseases or conditions characterized by insulin resistance, such as NIDDM and obesity, is inhibited by sodium salicylate (NaSal), prostaglandin derivatives (PPAR-γ agonists and PJG2) and a MAP kinase inhibitor. All of these compounds inhibited the MAP kinase pathway, in particular, ERK, and some of these compounds also inhibitied the JNK pathway. These findings indicate that TNF-α induced lipolysis and FFA release is mediated by the ERK pathway, and to a lesser extent by the JNK pathway. In addition, it was also shown that inhibition of the p38 pathway stimulates TNF-α induced lipolysis. Thus, the Examples described herein indicate that inhibition of the ERK/MAP kinase pathway and optionally the JNK pathway inhibit TNF-α induced lipolysis, whereas inhibition of the p38 pathway increases TNF-α induced lipolysis.

2. Definitions

For convenience, the meaning of certain terms and phrases employed in the specification, examples, and appended claims are provided below.

The term "activation of PPAR-γ" refers to the ability of a compound to selectively activate PPAR-γ-dependent gene expression, e.g., by increasing PPAR-γ-dependent transcription of a gene.

The term "agent" is used herein to denote a chemical compound, a mixture of chemical compounds, a biological macromolecule, or an extract made from biological materials such as bacteria, plants, fungi, or animal (particularly mammalian) cells or tissues. Agents can be evaluated for potential activity as antiproliferative agents by inclusion in screening assays described, for example, hereinbelow.

A "direct inhibitor" of a kinase is an inhibitor which interacts with the kinase or binding partner thereof or with a nucleic acid encoding the kinase.

A "disease or condition associated with TNF-α induced lipolysis" refers to a disease or condition which is caused, or contributed to, by lipolysis in adipose cells in response to TNF-α. Typically such diseases or disorders are caused by or contributed to by excessive free fatty acid and/or glycerol levels.

The term "ERK1/2" refers to ERK1 and/or ERK2, also referred to as "ERK."

The term "ERK pathway" also referred to herein as the "ERK/MAP kinase pathway" refers to a signal transduction pathway in which at least one ERK enzyme is involved.

The term "hyperinsulinemia" refers to a state in an individual in which the level of insulin in the blood is higher than normal.

The term "insulin resistance" refers to a state in which a normal amount of insulin produces a subnormal biologic response.

"Impaired glucose tolerance" or "IGT" is a condition intermediate between frank, NIDDM and normal glucose tolerance.

An "indirect inhibitor" of a kinase is an inhibitor which interacts upstream or downstream of the kinase in the regulatory pathway and which does not interacts with the kinase or binding partner thereof or with a nucleic acid encoding the kinase. Thus, for example, an indirect inhibitor of JNK can be an inhibitor of MEKK1.

The terms "induce", "inhibit", "potentiate", "elevate", "increase", "decrease" or the like, e.g., which denote quantitative differences between two states, refer to at least statistically significant differences between the two states. For example, "an amount effective to inhibit activation of a MAP kinase" means that the activation state of the MAP kinase will be at least statistically significantly different from the untreated cells.

An "inhibitor" of a kinase is any molecule which decreases the activity of the kinase or decreases the protein level of the kinase. Thus, a kinase inhibitor can be a small molecule which decreases activity of the kinase, e.g., by interfering with interaction of the kinase with another molecule, e.g., its substrate. It can also be a small molecule which decreases expression of the gene encoding the kinase. An inhibitor can also be an antisense nucleic acid, a ribozyme, an antibody, a dominant negative mutant of the kinase, or a phosphatase.

The term "JNK" or "JNK isoforms" includes both JNK-1 and JNK-2.

The term "JNK pathway" refers to a signal transduction pathway in which at least one JNK enzyme is involved.

The term "lipolysis" refers to the breakdown of triacylglycerol into glycerol and fatty acids, thereby resulting in the release of glycerol and free fatty acids from the cell.

The terms "mitogen activated protein kinase", "MAP kinase" and "MAPK" refer to protein kinases that are activated by dual phosphorylation on threonine and tyrosine and include among others: ERK1, ERK2, JNK-1, JNK-2, SAPK, p38, SMK1, HOG1, MPK1, FUS3/KSS1, and spk1.

The term "MAPK pathway" refers to a signal transduction pathway in which at least one MAP kinase is involved. This term includes "ERK pathways" and "JNK pathways."

The term "MAPK phosphatase" activity or function is the ability to dephosphorylate one or preferably both of the threonine and tyrosine residues on MAP kinase, which residues are phosphorylated in the activation of the MAP kinase.

The term "MKK" refers to MAPK kinase.

The term "MKK substrate" as used herein include MKK substrates, as well as MKK substrate substrates, e.g., p38, JNK, ATF2, and c-jun.

The term "PPAR-γ" refers to members of the peroxisome proliferator-activated receptors family which are expressed, inter alia, in adipocytic and hematopoietic cells (Braissant, O. et al. *Endocrinology* 137(1): 354–66), and which function as key regulators of differentiation. Contemplated within this definition are variants thereof, as for example, PPAR-γ1 and PPAR-γ2 which are two isoforms having a different N-terminal generated by alternate splicing of a primary RNA transcript (Tontonoz, P. et al. (1994), *Genes & Dev.* 8:1224–34; Zhu et al. (1993) *J. Biol. Chem.* 268: 26817–20).

As used herein, a "PPAR-γ agonist", that is useful in the method of the invention, refers to an agent which potentiates, induces or otherwise enhances the transcriptional activity of a PPAR receptor in a neoplastic cell. In certain embodiments, an agonist may induce activation of transcription by PPAR-γ transcriptional complexes, e.g., such as by mimicking a natural ligand for the receptor. In other embodiments, the agonist potentiates the sensitivity of the receptor to a PPAR-γ ligand, e.g., treatment with the agonist lowers the concentration of ligand required to induce a particular level of receptor-dependent gene activation.

As used herein, the term "PPAR-γ ligand", that is useful in the method of the invention, includes any naturally-occurring or non-naturally occurring agents that selectively and specifically binds to a PPAR-γ protein and upon binding, activates transcription of genes which contain a PPAR-γ responsive element. Examples of such ligands include, but are not limited to thiazolidinedione compounds, e.g., pioglitazone, troglitazone, BRL49653, and derivatives thereof, or prostaglandin (PG) metabotites, e.g., prostaglandin 15-deoxy-12,14 $PGJ_2$, and derivatives thereof.

"Signal transduction of a PPAR-γ receptor protein" is the intracellular processing of chemical signals that occur as a consequence of activation of the nuclear receptor, and may occur through one or more of several mechanisms, such as ligand binding, heterodimer complex formation, DNA binding and/or direct or indirect activation of transcription. Changes in the signal transduction pathway are ultimately detected by the increased expression of differentiation-specific genes and/or withdrawal from the cell cycle.

The term "TNF-α induced lipolysis" refers to TNF-α induced triacylglycerol degradation in an adipose cell, thereby resulting in the production of glycerol and free fatty acids (FFAs) in the cell which can be secreted from the cell.

The term "treating" or "treatment" of a subject having a disease or disorder refers to the improvement of at least one symptom of the disease or disorder.

3. Compounds which Inhibit TNF-α Induced Lipolysis

The invention provides methods for inhibiting or blocking lipolysis, e.g., in adipocytes. In a preferred embodiment, lipolysis is TNF-α induced lipolysis. In one embodiment, the compounds of the invention are modulators of MAP kinase pathways. Modulators of the invention also include sodium salicylate and agents which bind to the perixosome proliferator-activated receptor-γ (PPAR-γ).

I. Modulators of the MAP Kinase Pathways

Within the class of MAP kinase pathway modulators, i.e., activators and inhibitors, preferred compounds include inhibitors of the JNK pathway, inhibitors of the MAP/ERK pathway and stimulators of the p38 pathway. These compounds can be direct modulators, such as agents which interact directly with a kinase in MAP kinase pathways or nucleic acid encoding such, or an agent which interacts with a molecule (e.g., a protein) interacting with the kinase. Alternatively, the compounds of the invention can be indirect modulators of MAP kinase pathways. An indirect modulator of a specific kinase is an agent which does not interact with the kinase or a protein interacting therewith or nucleic acids encoding such. Preferred compounds of the invention are direct inhibitors of JNK-1, MAP kinases ERK1 or ERK2 and activators of p38.

Set forth below is a brief description of the three MAP kinase pathways and the kinases involved. Methods for modulating each of these pathways are set forth after this section. Proteins which modulate these pathways in cells are continuously being identified, and modulation of such proteins for the instant methods are also within the scope of the invention.

Mitogen-activated protein (MAP) kinases are a family of enzymes which regulate intracellular signaling pathways. MAP kinases are important mediators of signal transduction from cell surfaces to nuclei via phosphorylation cascades. Several subgroups of MAP kinases have been defined and each manifests different substrate specificities and responds to various distinct extracellular stimuli. Thus, the MAP kinase signaling pathways represent common mechanisms for signal transduction by which different extracellular stimuli generate distinct physiological responses inside cells (Egan S E and Weinberg R A (1993) *Nature* 365:781–783).

Various MAP kinase signaling pathways have been defined in mammalian cells as well as in yeast. In mammalian cells, the extracellular stimuli activating the MAP kinase signaling pathways include epidermal growth factor (EGF), ultraviolet light, hyperosmolar medium, heat shock, endotoxic lipopolysaccharide (LPS), and proinflammatory cytokines such as tumor necrosis factor (TNF) and interleukin-1(IL-1). In the yeast, *Saccharomyces cerevisiae*, various MAP kinase signaling pathways are activated by exposure to mating pheromone or hyperosmolarenvironments and during cell-wall construction, sporulation and mitosis. There are at least three subgroups of MAP kinases in mammalian cells (Derijard B et al (1995) *Science* 267:682–5), and each subgroup is distinguished by a tripeptide sequence motif. The subgroups are extracellular signal-regulated protein kinase (ERK) characterized by Thr-Glu-Tyr, c-Jun amino-terminal kinase (JNK) characterized by Thr-Pro-Tyr, and p38 kinase characterized by Thr-Gly-Tyr. The subgroups are activated by the dual phosphorylation of the threonine and tyrosine by MAP kinase kinases (MKK) located upstream of the phosphorylation cascade. Activated MAP kinases phosphorylate other effectors downstream ultimately leading to changes inside the cell.

c-Jun amino-terminal kinases (JNKs), or stress-activated protein kinases (SAPKs), are members of the mitogen-activated protein (MAP) kinase group which are activated in response to cytokines, such as TNF, e.g., TNF-α and IL-1, and exposure to environmental stress, including ultraviolet light, heat shock, and osmotic stress (U.S. Pat. No. 5,605, 808; B. Derijard et al., *Cell* 176,1025 (1994); J. M. Kyrakis et al, *Nature* 369, 156 (1994)). The Ras proteins may partially activate the JNK signal transduction pathway. An analysis of a deduced primary sequence of the two isoforms of JNK, JNK-1 which is a 46 kDa protein and JNK-2, which is a 55 kDa, reveals that they are distantly related to the ELK subgroup.

Substrates of the JNK protein kinase include the transcription factors ATF2, Elk-1, and c-Jun (A. J. Whitmarsh and R. J. Davis, J. Mol Med. 74, 589 (1996)). JNK phosphorylates each of these transcription factors within the activation domain and increases transcriptional activity (A. J. Whitmarsh, supra). For example, JNKs phosphorylate Ser63 and Ser73 in the amino-terminal domain of the transcription factor c-Jun which results in increased transcriptional activity.

Genetic studies of JNK indicate that this signaling pathway is involved in multiple cellular processes (H. K. Sluss, Z. Han, T. Barrett, R J. Davis, T., *Genes Dev.* 10, 2745 (1996); J. R Riesgo-Escovar, M. Jenni, A. Fritz, E. Hafen, ibid., p. 2759).

JNKs are activated by dual phosphorylation at Thr183 and Tyr185 within the motifs Thr-Glu-Tyr and Thr-Pro-Tyr, respectively, by MKK4 (including MKK4-α, -β, and -γ) and MAP kinase kinases (Davis R (1994) *TIBS* 19:470–473 and PCT application having publication No. WO 96/36642 by Davis et al.).

Although JNK is located in both the cytoplasm and the nucleus of quiescent cells, activation of JNK is associated with accumulation of JNK in the nucleus (M. Cavigelli, F. Dolfi, F.-X. Claret, M. Karin, *EMBO J.* 14, 5957 (1995)). A murine cytoplasmic protein that binds specifically to JNK [the JNK interacting protein-1 (JIP-1)] was characterized and cloned (Dickens et al. (1997) *Science* 277: 693). JIP-1 caused cytoplasmic retention of JNK, as shown by overexpression of JIP-1, which caused retention of JNK in the cytoplasm. JIP-1 also caused inhibition of JNK-regulated gene expression. In addition, JIP-1 suppressed the effects of the JNK signaling pathway on cellular proliferation.

The ERK signal transduction pathway is activated via tyrosine kinase receptors on the plasma membrane of the cell. When EGF or other growth factors bind to the tyrosine receptors, they, in turn, bind to noncatalytic, src homology (SH) adaptor proteins (SH2-SH3-SH2) and a guanine nucleotide releasing protein. The latter reduces GTP and activates Ras proteins, members of the large family of guanine nucleotide binding proteins (G-proteins). The activated Ras proteins bind to a protein kinase C-Raf-1 and activate the Raf-1 proteins. The activated Raf-1 kinase subsequently phosphorylates MAP kinase kinases which, in turn, activate MAP kinase ERKs by phosphorylating the threonine and tyrosine residues of the ERKs.

ERKs are proline-directed protein kinases which phosphorylate Ser/Thr-Pro motifs. In fact, cytoplasmic phospholipase A2 (cPLA2) and transcription factor Elk-1 are substrates of the ERKs. The ERKs phosphorylate Ser505 cPLA2 and cause an increase in its enzymatic activity resulting in an increased release of arachidonic acid and the formation of lysophospholipids from membrane phospholipids. Likewise, phosphorylation of the transcription factor Elk-1 by ERK ultimately results in increased transcriptional activity.

ERK-1 is a 44 kDa protein and ERK-2 is a 42 kDa protein. Activation of these MAP kinases requires an ordered phosphorylation of a threonine and tyrosine located within the conserved kinase subdomain 8 (T183 and Y185).

ERK activity is regulated by the mitogen-induced dual specificity phosphatases MKP1 and PAC1 (Ward et al. (1994) *Nature* 367:651). Another phosphatase which dephosphorylates both serine/threonine and tyrosine residues and of which erk2 is a substrate is encoded by the human gene CL100 and its murine counterpart 3CH134 (Charles et al. (1992) *Oncogene* 7:187). When expressed in vitro, this gene has been shown to be very specific for MAP kinase and leads to the dephosphorylation and inactivation of MAP kinase (Charles et al. (1993) *PNAS* 90:5292). WO 95/21923 by Ashworth et al. also discloses the cloning of MAP kinase phosphatases, which are capable of dephosphorylating erk2.

p38 is a 41 kD protein containing 360 amino acids which is activated by heat shock, hyperosmolar medium, IL-1 or LPS endotoxin (Han J et al (1994) *Science* 265:808–811) produced by invading gram-negative bacteria p38 is activated by dual phosphorylation at Thr180 and Tyr182 within the motif Thr-Gly-Tyr and once activated, p38 phosphorylates MBP and EGF-R and to a lesser extent IkB, but not cytoplasmic phospholipase A2, c-Myc nor c-Jun (Davis et al., supra).

p38 is phosphorylated by MKK, which exists as isoforms MKK3, MKK6, and MKK4 (including MKK4-α, -β, and -γ). These kinases have serine, threonine, and tyrosine kinase activity, and specifically phorphorylate the human MAP kinase p38 at Thr180 and Tyr182. The amino acid and nucleotide sequences of MKK3, MKK4, and MKK6 are set forth in published PCT application having publication No. WO 96/36642 by Davis et al. *P*38 activity is regulated by the mitogen-induced dual specificity phosphatases MKP1 and PAC1 (Davis et al., supra).

In one embodiment of the invention, an inhibitor of JNK or ERK/MAP kinase pathways is a compound which blocks, reduces or decreases the activity of a kinase in these pathways or the activity of a protein regulating the kinases. For example, the compound can inhibit activation of the kinase by inhibiting phosphorylation of the kinase, such as by inhibiting the interaction between the kinase and the kinase that phosphorylates it. In fact, as described herein, kinases from the MAP kinase pathways are active only when they are phosphorylated, usually on two residues. Thus, in one embodiment, the compound of the invention is a compound which interferes with the interaction between JNK and MKK4 or between ERK and MEK. The compound can be a small molecule. Alternatively, the compound can be a dominant negative form of JNK or MKK4 or of a MAP kinase, e.g., ERK or MEK. A catalytically inactive JNK-1 molecule functioning as a dominant inhibitor of the wild-type JNK-1 molecule is described, e.g., in Example 13 of PCT application having publication No. WO 96/36642 by Davis et al. This mutant was constructed by replacing the sites of activating Thr183 and Tyr185 phosphorylation with Ala and Phe, respectively. As shown in Davis et al., this dominant negative mutant effectively blocked phosphorylation by wild-type JNK-1 of the substrate ATF2.

Dominant negative mutants of Ras, Raf-1, ERK-1, and ERK-2 (i.e., RasN17, Raf301, ERK(K71R), and ERK (K52R), respectively) are described, e.g., in Li et al. *Mol Cell Biol* (1996) 16:5947. A dominant negative mutant of Ras is described, e.g., in Zou et al. *J Biol Chem* (1996); 271:33592. Dominant negative forms of ERK proteins, and upstream or downstream kinases thereof can also be used in the invention. Dominant negative mutants of ERKS, MEKs, and other MAP kinases, e.g., Ras, Rac, and Raf are known in the art For example, Bjorkoy et al., (1997) *PNAS* 272 (17):11557 describes a dominant negative lambdaPKC that abolishes nuclear ERK activation. A dominant-negative MEKK1 or MKK4/SEK mutant is described, e.g., in Hu et al. *Genes Dev* (1996) 10:2251 and in Ben et al., *J Virol* (1996) 70:4978. A dominant negative mutant of the ERK-specific regulator MEK1 is described, e.g., in Pestell et al., *Mol Endocrinol* (1996) 10:1084. Adenoviral vectors expressing dominant negative mutants are described, e.g., in Gabbay et al. *J Biol Chem* (1996); 271:1890 (adenovirus vector encoding a dominant-negative mutant of Ras) and Auer et al. *Mol Biol Cell* (1998); 9:561 (adenoviruses encoding dominant negatives Ras N17, Rac1 (N17), Cdc42 (N17), SEK1-, and JNK1). Other dominant negative mutants of the MAPK and JNK pathways can be designed according and tested out according to methods known in the art, such as those that were used to create the mutants described here.

The activity of a kinase can also be reduced by inhibiting or reducing the interaction between the kinase and a substrate of the kinase or by inhibiting phosphorylation of the substrate. For example, the activity of JNK can be inhibited by a compound which interferes with the interaction between a JNK and c-jun. The compound can be a small molecule. The compound can also be a dominant negative form of JNK or c-jun.

In another embodiment, the activity of a kinase is inhibited by dephosphorylating the kinase, Dephosphorylation can be accomplished, e.g., by phosphatases. Thus, in one embodiment of the invention, a phosphatase is introduced into a target cell, e.g., by expression of a nucleic acid encoding the phosphatase in the target cell. Expression of a phosphatase can be limited to specific tissues, e.g., by using a tissue specific promoter, or by using a vehicle targeting the gene to a specific tissue. MAP kinase specific phosphatases have been described. For example, MKP1 and PAC1 (Ward et al. (1994) *Nature* 367:651) are phosphatases which specifically inactivate Erk2 and p38 (see infra). As set forth above, CL100 specifically dephosphorylates and inactivates Erk2.

In yet another embodiment, the activity of a kinase in a cell is modulated, e.g., inhibited, by modulating expression of the gene encoding the kinase. In an exemplary embodiment, the expression of the gene is modulated by modulating transcription of the gene, such as with compounds which affect a regulatory element within the gene. Such compounds are described in the literature. Gene transcription of a specific gene encoding a MAP kinase, e.g, a JNK, can also be inhibited by using the triplex technology, further described below.

Alternatively, the amount of a MAP kinase or protein regulating a MAP kinase is modulated in a cell with antibodies, e.g., intracellular antibodies, e.g., single chain antibodies. Methods for preparing antibodies are further described herein.

Expression of a MAP kinase gene can also be inhibited by using antisense nucleic acids. Such nucleic acids are commercially available for some MAP kinases. For example, an antisense oligonucleotide inhibiting production of ERK1 and ERK2 is available from BIOMOL Research Laboratories, Inc. (Plymouth Meeting, Pa.; catalog #). The antisense oligonucleotide is a 17-mer oligodeoxynucleotide with all phosphorothioate linkages. It is directed against a sequence which is identical in the p42 and p44 MAP kinase isoforms (ERK2, ERK1) and conserved in human, mouse and rat (E. M. Sale et al. *EMBO J.* 1995 14 674). There was no effect on expression of the MAP kinase homologs, p38 and JNK, and no effect on MEK activation (C. J. M. Robinson et al. *Biochem. J.* 1996 320 123). Antisense nucleic acids can also be prepared as further described herein. In yet another embodiment, mRNA encoding the MAP kinase is degraded by use of a ribozyme, as further described herein.

In yet another embodiment, the activity of a kinase is regulated by regulating its cellular localization. Thus, it has been shown that a cytoplasmic protein that binds specifically to JNK (JIP-1) caused cytoplasmic retention of JNK, thereby resulting in inhibition of JNK-regulated gene expression. Thus, the activity JNK in a cell can be inhibited by contacting the cell with an agent which causes retention of JNK in the cytoplasm. This can be achieved, e.g., by expressing JIP-1 in a cell.

The nucleic acid sequences of the MAP kinases are available in the literature as well as in GenBank. Furthermore, recombinantly produced MAP kinases and substrates are available commercially. These can be used, e.g., to identify compounds modulating the activity of MAP kinases. For example, recombinant JNK (rat) is available from BIOMOL Research Laboratories, Inc. (Plymouth Meeting, Pa.; catalog # SE-150). A GST-fusion protein of the c-jun (1-79) activation domain is commercially available from BIOMOL Research Laboratories, Inc. (Plymouth Meeting, Pa.; catalog # SE-151).

Antibodies against members of the MAP kinase families are available commercially, e.g., from BIOMOL Research Laboratories, Inc. (Plymouth Meeting, Pa.), Chemicon International, Inc. (Temecula, Calif.), Calbiochem (La Jolla), and Sigma Chemical Co. (St. Louis, Mo.). Antibodies to Erk kinases are described, e.g., in European patent application EP 0 735 370 by Takeda Chemical Industries, Ltd.

In a specific embodiment in which the modulator is encoded by a nucleic acid which is delivered to a target cell, it is desirable to operably link the nucleic acid encoding the inhibitor to regulatory elements allowing transcription of the nucleic acid in appropriate conditions. Regulatory elements is intended to include promoters, enhancers, silencers, and polyadenylation sequences. The nucleic acid encoding the inhibitor is also preferably inserted into a plasmid, to thereby generate an expression vector. Expression vectors containing appropriate regulatory elements for expression in eukaryotic cells are available commercially.

II. Other Compounds of the Invention

Other preferred compounds of the invention include compounds which inhibit TNF-α. Such compounds include those which inhibit the production of TNF-α, as well as those which specifically inhibit its activity, e.g., by interfering with its interaction with a receptor. For example, an inhibitor can be an antibody binding specifically to, and inhibiting the activity of, TNF-α. Yet other inhibitory compounds include inhibitors of a TNF-α receptor or of a molecule interacting therewith, such as the MADD protein (Schievella et al. (1997) *J. Biol. Chem.* 272:12069). Thus, within the scope of the invention are antisense and triplex molecules which specifically inhibit the expression of TNF-α a TNF-α receptor, or molecule interacting with TNF-α or its receptor, such as MADD.

Another preferred compound for use in the methods of the invention include sodium salicylate (NaSal) and derivatives thereof. As described in the Examples, NaSal has in fact been shown herein to inhibit JNK activation by TNF-α in adipocytes and to inhibit TNF-α induced lipolysis in adipocytes. NaSal has also been described as being capable of inhibiting TNF-induced activation of JNK and p42/1p44 MAP kinases in FS4 fibroblasts (Schwenger et al. (1997) *P.N.A.S. USA* 94:2869) and Schwenger et al. (1996) *J. Biol. Chem.* 271:8089, respectively).

Also within the scope of the invention are compounds which are naturally occuring or non-naturally occurring agonists of the peroxisome proliferator-activated receptor-γ (PPAR-γ). These agents are often capable of promoting differentiation of adipocytes. Preferred PPAR-γ agonists include prostaglandins, thiazolidinediones, prostaglandin derivatives including prostanoids, such as 15-deoxy-12,14-prostaglandin J2 (referred to as "PGJ2"), and a variety of non-steroidal anti-inflammatory drugs (NSAIDs) (Lechman et al. (1997) *J. Biol. Chem.* 272:3406).

Particular examples of a non-naturally occurring PPAR-γ ligand include thiazolidine (TZD) derivatives known as thiazolidinediones, e.g., proglitazone (also known as AD-4833 and U-72107E), troglitazone (also known as CS-045) (Sankyo) and C1-991 (Parke-Davis), BRL 49653 (rosiglitazone), ciglitazone, englitazone and chemical derivatives thereof. See, e.g., in U.S. Pat. Nos. 4,812,570; 4,775,687; 4,725,610; 4,582,839; and 4,572,912 for exemplary sources of such compounds. U.S. Pat. No. 5,521,201 and European Patent Applications 0008203, 0139421, 0155845, 0177353, 0193256, 0207581 and 0208420, and *Chem Pharm. Bull* 30 (10) 3580–3600 relate to thiazolidinedione derivatives, and describe commercial sources/synthetic schemes for a variety of TZD and TZD-like analogs, which may be useful in carrying out the method of the present invention.

Particular examples of naturally-occuring PPAR-γ ligands include arachidonic acid metabolites, e.g., prostaglandin $J_2$ (PGJ2) metabolites, e.g., 15-deoxy-$^{12,14}$-prostaglandin $J_2$. Prostaglandin J2 dehydration and isomerization products, including $^{12}$-$PGJ_2$ and 15-deoxy-$^{12,14}$-$PGJ_2$ have been shown to occur by incubation of prostaglandin $D_2$ ($PGD_2$) in the presence of human plasma or human serum albumin (Fitzpatrick and Wyvalda (1983) J. Biol. Chem. 258:11713–18). $^{12}$-$PGJ_2$ has been shown to be a significant $PGD_2$ metabolite present in human and monkey urine, indicating that $PGJ_2$ metabolites are also found in vivo (Hirata et al. (1994) PNAS USA 91:11192–96).

Examples of PPAR-γ agonists are also disclosed in PCT publications WO 91/07107; WO 92/02520; WO 94/01433; WO 89/08651; WO 95/18533; WO 95/35108; Japanese patent publication 69383/92; and U.S. Pat. Nos. 5,523,314; 5,521,202; 5,510,360; 5,498,621; 5,496,621; 5,494,927; 5,480,896; 5,478,852; 5,468,762; 5,464,856; 5,457,109; 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445.

Exemplary PPAR-γ agonists can be selected from amongst such compounds as 5-[4-[2-(5ethylpyridin-2-yl)ethoxyl]benzyl]thiadiazolidine-2,4-dione: (pioglitazone); 5-[4-[(1-methylcyclohexyl)methoxy]benzyl]thiadiazolidine-2,4-dione: (ciglitazone); 5-[(2-benzyl-2,3-dihydrobenzopyran)-5-ylmethyl]thiadiazoline-2,4-dione: (englitazone); 5-[(2-alkoxy-5-pyridyl)methyl]-2,4-thiazolidinedione; 5-[(substituted-3-pyridyl)methyl]-2,4-thiazolidinedione; 5-[4-(2-methyl-2-phenylpropoxy)benzyl]thiazolidine-2,4-dione; 5-[4-[3-(4-methoxyphenyl)-2-oxooxazolidin-5-yl]-methoxy]benzyl-2,4-thiazolidinedione; 5-[4-[3-(3,4-difluorophenyl)-2-oxooxazolidin-5-yl]-methoxy]benzyl-2,4-thiazo-lidinedione; 5-[4[3-(4-chloro-2-fluorophenyl)-2-oxooxazolidin-5-yl]methoxy]benzyl-2,4-thiazolidinedione; 5-[4-[3-(4-trifluoromethoxyphenyl)-2-oxooxazolidin-5-yl]methoxy]benzyl-2,4-thiazolidinedione; 5-[4-[3-(4-trifluoromethylphenyl)-2-oxooxazolidin-5-yl]methoxy]benzyl-2,4-thiazolidinedione; 5-[4-[2-[3-4-trifluoromethylphenyl)-2-oxooxazolidin-5-yl]ethoxy]benzyl]-2,4-thiazolidinedione; 5-[4-[2-[3-(4-chloro-2-fluorophenyl)-2-oxooxazolidin-5-yl]ethoxy]benzyl]-2,4-thiazolidinedione; 5-[4-[3-(4-pyridyl)-2-oxooxazolidin-5-yl]methoxy]-benzyl-2,4-thiazolidinedione; 5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone); 4-(2-naphthylmethyl)-1,2,3,5-oxathiadiazole-2-oxide; 5-[4-[2-[N-(benzoxazol-2-yl)-N-methylamino]ethoxy]benzyl]-5-methylthiazolidine-2,4-dione; 5-[4-[2-[2,4-dioxo-5-phenylthiazolidin-3-yl)ethoxy]benzyl]thiazolidine-2,4-dione; 5-[4-[2-[N-methyl-N-(phenoxycarbonyl)amino]ethoxy]benzyl]thiazolidine-2,4-dione; 5-[4-(2-phenoxyethoxy)benzyl]thiazolidine-2,4-dione; 5-[4-[2-(4-chlorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiadiazolidine-2,4-dione; 5-[4-[2-(5-methyl-2-phenyloxazol-4-yl)ethoxyl]benzyl]thiadizolidione-2,4-dione; 5-[[2-(2-naphthylmethyl)benzoxazol]-5-ylmethyl]thiadiazolidine-2,4-dione; 5-[4-[2-(3-phenylureido)ethoxyl]benzyl]thiadiazoline-2,4-dione; 5-[4-[2-[N-(benzoxazol-2-yl)-N-methylamino]ethoxy]benzy]thiadiazoline-2,4-dione; 5-[4-[3-(5-methyl-2-phenyloxazol-4-yl)propionyl]benzyl] thiadiazoline-2,4-dione; 5-[2-(5-methyl-2-phenyloxazol-4-ylmethyl)benzofuran-5-ylmethyl]-oxazolidine-2,4-dione; 5-[4-[2-[N-methyl-N-(2-pyridyl)amino]ethoxy]benzyl] thiazolidine-2,4-dione; and 5-[4-[2-[N-(benzoxazol-2-yl)-N-methylamino]ethoxy]benzyl]-oxazolidine-2,4-dione.

Other PPAR-γ agonists can be identified by methods known in the art. Such methods can, in particular, be used to screen libraries of compounds.

In another embodiment, the subject methods combines the use of PPAR-γ agonists in combination with one or more modulators of MAP kinase pathways. For instance, the subject method can be practiced by conjoint treatment using a PPAR-γ agonist as described above and an inhibitor of JNK-1. The term "in combination" in this context means that the drugs are given substantially contemporaneously, either simultaneously or sequentially. If given sequentially, at the onset of administration of the second compound, the first of the two compounds is preferably still detectable at effective concentrations at the site of treatment.

Also contemplated are chemicals that stimulate the endogenous production of arachidonic acid metabolites, when administered systemically or in vitro. Enhanced production of endogenous arachidonic acid metabolites may occur by stimulating at least one of the release of arachidonic acid from precursor glycerophospholipids, the oxygenation of free arachidonic acid by a cyclo-oxygenase enzyme, and the metabolism of prostaglandin $H_2$ to a specific biologically active prostaglandin metabolite (reviewed in Smith, W. (1989) Biochem. J., 259:315–24).

In general, it will be preferable to choose a PPAR-γ agonist which specifically activates that PPAR isoform relative to, for example, PPAR-α and/or PPAR-δ. According to this present invention, specificity for the PPAR-γ isoform can reduce unwanted side effects, such as PPAR-α mediated hepatocarcinogenesis. In particular, the PPAR-γ agonist of the present method preferably activates PPAR-γ-dependent transcription at a concentration at least 1 order of magnitude less than that which activates PPAR-α-dependent transcription, and even more preferably at a concentration at least 2, 3, 4 or 5 orders of magnitude less.

In a preferred embodiment, the compounds of the invention, e.g., JNK-1 inhibitors are cell type specific. Thus, for example, a compound can be targeted to a site where lipolysis occurs. Targeting can be achieved by delivering the compound in a vehicle that will specifically recognize certain cell types. For example, the delivery vehicle can be linked to an antibody that binds to an antigen on the surface of the target cell. Alternatively, the compound itself is linked to a targeting molecule, e.g., an antibody. Where the inhibitor is a protein encoded by a nucleic acid which is delivered to a cell, specificity can be achieved by using a cell type specific regulatory element, to thereby limit expression is specific types of cells. Such regulatory elements are well known in the art.

4. Antisense, Ribozymes, and Triplex Techniques

Set forth below is a description on how to design and prepare antisense and ribozymes, for modulating the activity of MAP kinase pathways, in particular, to inhibit the JNK and MAP/ERK kinase pathways and/or to stimulate the p38 pathway. The invention also provides antisense and ribozymes for blocking expression of negative regulators of PPAR-γ. The nucleotide and amino acid sequences of the subject kinases are set forth above and the teaching set forth below apply generally to these nucleic acids.

As used herein, "antisense" therapy refers to administration or in situ generation of oligonucleotide molecules or their derivatives which specifically hybridize (e.g., bind)

under cellular conditions, with the cellular mRNA and/or genomic DNA encoding a member of the MAP kinase pathways or protein regulating such, so as to inhibit expression of the member of the MAP kinase pathway or protein regulating such, e.g., by inhibiting transcription and/or translation. The protein against which an antisense molecule is prepared is termed herein "target protein" and the gene encoding the target protein is referred to as the "target gene". The antisense is selected to inhibit the JNK and/or the ERK/MAP kinase pathways or to stimulate the p38 pathway. The binding of the antisense molecule may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a target protein. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *BioTechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the target nucleotide sequence of interest, are preferred.

Antisense approaches involve the design of oligonucleotides (either DNA or RNA) that are complementary to a target mRNA. The antisense oligonucleotides will bind to the target mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R 1994. *Nature* 372:333). Therefore, oligonucleotides complementary to either the 5' or 3' untranslated, non coding regions of a gene of interest could be used in an antisense approach to inhibit translation of endogenous mRNA of interest. Oligonucleotides complementary to the 5' untranslated region of the mRNA preferably should include the complement of the AUG start codon. Antisense oligonucleotides complementary to mRNA coding regions are less efficient inhibitors of translation but could also be used in accordance with the invention. Whether designed to hybridize to the 5', 3' or coding region of the target mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety; sugar moiety, or phosphate backbone, for example, to improve stability of the molecule, hybridization, etc. The oligonucleotide may include other appended groups such as peptides (e.g., for targeting host cell % receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl Acids Re. 16:3209), methylphosphonate olgonucleotides can be prepared by use of controlled pore glass polymer supports (Sarin et al., 1988, Proc. Natl. Acad. Sci. U.S.A. 85:7448–7451), etc.

In another embodiment, the antisense molecule is stablilized by the addition of flanking sequences of ribonucleotides or deoxyribonucleotides to the 5' and/or 3' of the molecule.

While antisense nucleotides complementary to the coding region of the target gene can be used, those complementary to the transcribed untranslated region and to the region comprising the initiating methionine are most preferred.

The antisense molecules can be delivered to cells which express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target transcripts and thereby prevent translation of the target mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Ribozyme molecules designed to catalytically cleave mRNA transcripts of interest, e.g., MAPK mRNA transcripts, can also be used to prevent translation of target mRNA and expression of target proteins (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are a number of potential hammerhead ribozyme cleavage sites within the nucleotide sequence of human target. Preferably the ribozyme is engineered so that the cleavage recognition site is located near the 5' end of the target mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574–578; Zaug and Cech, 1986, Science, 231:470475; Zaug, et al., 1986, Nature, 324:429433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a MAPKgene.

As in the antisense approach, the ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express target in viva. Insertion of the DNA construct, via targeted homologous recombination, results in inactivation of the target gene. Such approaches are particularly suited in the agricultural field where modifications to ES (embryonic stem) cells can be used to generate animal offspring with an inactive MAPK (e.g., see Thomas & Capecchi 1987 and Thompson 1989, supra). However this approach can be adapted for use in humans provided the recombinant DNA constructs are directly administered or targeted to the required site in viva using appropriate viral vectors.

Alternatively, endogenous target gene expression can be reduced by targeting deoxyribonucleotide sequences complementary to the regulatory region of the target gene (i.e., the target promoter and/or enhancers) to form triple helical structures that prevent transcription of the target gene in target cells in the body. (See generally, Helene, C. 1991, Anticancer Drug Des., 6(6):569–84; Helene, C., et al., 1992, Ann. N.Y. Acad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Ribozyme and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, ribozymes and triplex molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, ribozyme and triplex molecule constructs that encode ribozymes or triplex molecules constitutively or inducibly, depending on the promoter used, can be introduced stably into cell lines. These techniques are further described herein in relation to antisense molecules.

Moreover, various well-known modifications to nucleic acid molecules may be introduced as a means of increasing intracellular stability and half-life. Possible modifications include but are not limited to the addition of flaking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

5. Antibodies for Use in the Invention

Antibodies binding specifically to certain MAP kinases can be used to inhibit activation of MAP kinases according to the methods of the invention. Antibodies can also be used for detecting MAP kinases and for use in assays for isolating compounds which inhibit the activity of MAP kinases. Other antibodies within the scope of the invention are antibodies which bind to and activate the PPAR-γ receptor.

Anti-MAP kinase antibodies are commercially available. However, antibodies, including anti-PPAR-γ antibodies can also be prepared according to methods known in the art. For example, by using immunogens derived from a MAP kinase protein or a PPAR-γ receptor, e.g., those based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian target polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a target protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a JNK of a mammal.

Following immunization of an animal with an antigenic preparation of a target polypeptide, anti-target polypeptide antisera can be obtained and, if desired, polyclonal anti-target polypeptide antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBVhybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian target polypeptide of the present invention and monoclonal antibodies isolated from a culture comprising such hybridoma cells.

The term antibody as used herein is intended to include fragments thereof which are also specifically reactive with a mammalian MAP kinase or a PPAR-γ. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric, and humanized molecules having affinity for an MAP kinase conferred by at least one CDR region of the antibody. Other preferred antibody molecules include intracellular antibodies, e.g., single chain antibodies. Such antibodies can, e.g., inhibit the activity of an ERK and/or JNK kinase or upstream or downstream kinase in their pathways. Production and use of such antibodies is known in the art, as well as gene therapy methods for administering to a subject construct(s) encoding such.

6. Methods for Identifying Modulators of the Kinase Pathways

Modulators of kinase pathways can be identified in cell based assays or in in vitro assays. In a preferred embodiment, a modulator is identified by screening for compounds which are capable of inhibiting the interaction between a kinase, e.g., JNK-1, and a protein interacting with it (referred to as "binding partner"), such as a substrate of a protein acting upstream of the kinase, and which e.g., phosphorylates or dephosphorylates the kinase. Alternatively, an in vitro kinase assay comprising a kinase and a substrate or upstream kinase, can be performed and test compounds added to the reaction. Such a reaction can be performed as described in the Examples.

In addition, cell free assays can be used to identify compounds which are capable of interacting with a kinase or binding partner, to thereby modify the activity of the kinase or binding partner. Such a compound can, e.g., modify the structure of a kinase or binding partner and thereby effect its activity.

Accordingly, one exemplary screening assay of the present invention includes the steps of contacting a kinase or functional fragment thereof or a kinase binding partner with a test compound or library of test compounds and detecting the formation of complexes. For detection purposes, the molecule can be labeled with a specific marker and the test compound or library of test compounds labeled with a different marker. Interaction of a test compound with a kinase or fragment thereof or kinase binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the kinase, functional fragment thereof, or binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) a kinase or portion thereof, (ii) a kinase binding partner (e.g., substrate or directly upstream kinase), and (iii) a test compound; and (b) detecting interaction of the kinase and the kinase binding protein. The kinase and kinase binding partner can be produced recombinantly, purified from a source, e.g., plasma, or chemically synthesized, as described herein. A statistically significant change (potentiation or inhibition) in the interaction of the kinase and kinase binding protein in the presence of the test compound, relative to the interaction in the absence of the test compound, indicates a potential agonist (mimetic or potentiator) or antagonist (inhibitor) of kinase bioactivity for the test compound. The compounds of this assay can be contacted simultaneously. Alternatively, a kinase can first be contacted with a test compound for an appropriate amount of time, following which the kinase binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified kinase or binding partner is added to a composition containing the kinase binding partner or kinase, and the formation of a complex is quantitated in the absence of the test compound.

Complex formation between a kinase and a binding partner may be detected by a variety of techniques. Modulation of the formation of complexes can be quantitated using, for example, detectably labeled proteins such as radiolabeled, fluorescently labeled, or enzymatically labeled kinases or binding partners, by immunoassay, or by chromatographic detection.

Typically, it will be desirable to immobilize either the kinase or its binding partner to facilitate separation of complexes from uncomplexed forms of one or both of the proteins, as well as to accommodate automation of the assay. Binding of kinase to a binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/kinase (GST/kinase) fusion proteins can be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of kinase or binding partner found in the bead fraction quantitated from the gel using standard electrophoretic techniques such as described in the appended examples.

Other techniques for immobilizing proteins on matrices are also available for use in the subject assay. For instance, either the kinase or its cognate binding partner can be immobilized utilizing conjugation of biotin and streptavidin. For instance, biotinylated kinase molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the kinase can be derivatized to the wells of the plate, and the kinase trapped in the wells by antibody conjugation. As above, preparations of a binding protein and a test compound are incubated in the kinase presenting wells of the plate, and the amount of complex trapped in the well can be quantitated. Exemplary methods for detecting such complexes, in addition to those described above for the GST-immobilized complexes, include immunodetection of complexes using antibodies reactive with the binding partner, or which are reactive with the kinase and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the binding partner. To illustrate, the binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2, 4-dinitrobenzene (Habig et al (1974) *J Biol Chem* 249:7130).

For processes which rely on immunodetection for quantitating one of the proteins trapped in the complex, antibodies against the protein, such as anti-JNK-1 antibodies, can be used. Alternatively, the protein to be detected in the complex can be "epitope tagged" in the form of a fusion protein which includes, in addition to the kinase sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharmacia, N.J.).

Other assays for identifying MAP kinase modulators include cell based assays. In an exemplary embodiment, a cell expressing a kinase of interest, e.g., JNK-1, is incubated with a test compound, and the activity of the kinase is measured, e.g., by measuring JNK-1 phosphorylation or phosphorylation of a JNK-1 substrate. Detection can be done on isolated protein or on the cell.

In certain embodiments, the kinase inhibitors are derivatives of MAP kinases, such as dominant negative mutants. Such mutants can be obtained by screening libraries of MAP kinase analogs, such as MAP kinases having amino acid substitutions. In one embodiment, the variegated library of kinase variants is generated by combinatorial mutagenesis at the nucleic acid level, and is encoded by a variegated gene library. For instance, a mixture of synthetic oligonucleotides can be enzymatically ligated into gene sequences such that the degenerate set of potential kinase sequences are expressible as individual polypeptides, or alternatively, as a set of larger fusion proteins (e.g., for phage display) containing the set of kinase sequences therein.

There are many ways by which such libraries of potential kinase homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential kinase sequences. The synthesis of degenerate oligonucleotides is well known in the art (see for example, Narang, S A (1983) *Tetrahedron* 39:3; Itakura et al. (1981) *Recombinant DNA, Proc 3$^{rd}$ Cleveland Sympos. Macromolecules*, ed. AG Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a kinase clone in order to generate a variegated population of kinase fragments for screening and subsequent selection of inhibitors such as dominant negative forms of the kinase. A variety of techniques are known in the art for generating such libraries, including chemical synthesis. In one embodiment, a library of coding sequence fragments can be generated by (i) treating a double stranded PCR fragment of an kinase coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate kinase sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2, In Maenner and Manderick, eds., Elsevir Publishing Co., Amsterdam, pp. 401–410; Delgrave et al., 1993, Protein Engineering 6(3):327–331).

The invention also provides for reduction of the kinase proteins to generate mimetics, e.g., peptide or non-pepide agents, such as small molecules, which are able to disrupt binding of a kinase of the present invention with a molecule, a substrate. Thus, such mutagenic techniques as described above are also useful to map the determinants of the kinases which participate in protein-protein interactions involved in, for example, binding of the subject kinases to a substrate. To illustrate, the critical residues of a subject kinases which are involved in molecular recognition of its binding partner, e.g., substrate, can be determined and used to generate kinase derived peptidomimetics or small molecules which competitively inhibit binding of the authentic kinase with that moiety. By employing, for example, scanning mutagenesis to map the amino acid residues of the subject kinase proteins which are involved in binding other proteins, peptidomimetic compounds can be generated which mimic those residues of the kinase which facilitate the interaction. Such mimetics may then be used to interfere with the normal function of a kinase. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R Marshall ed., ESCOM Publisher: Leiden, Netherlands, 1988), keto-methylene pseudopeptides (Ewenson et al. (1986) *J Med Chem* 29:295; and Ewenson et al. in Peptides: Structure and Function (Proceedings of the 9$^{th}$ American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and Dann et al. (1986) *Biochem Biophys Res Commun* 134:71). Assays for testing the activity of the compounds of the various combinatorial libraries, including kinase assays are described herein.

The compounds identified as being modulators of kinase pathways, e.g., JNK-1 inhibitors, can then be tested in a lipolysis assay. Alternatively, compounds can first be identified directly in a lipolysis assay. Assays for determining whether a compound is capable of inhibiting lipolysis or to screen libraries of compounds for those capable of inhibiting lipolysis are described herein in the examplification. Briefly, adipocytes, e.g., 3T3-L1 fibroblasts induced to differentiate into adipocytes, are preincubated with a test compound for a certain number of hours before being contacted with an agent which induces lipolysis, e.g., TNF-α for a certain number of hours. The amount of glycerol of FFA in the cell medium is then measured, as described in the examples.

Set forth below are other lipolysis assays that can be used. Assays can be performed using 3T3-L1 fibroblasts which can be induced to differentiate into adipocytes (ATCC No. CL-173; and described in U.S. Pat. No. 4,003,789 and in Cell 3:127 (1974)). Alternatively, assays can be performed using freshly isolated adipocytes, e.g., as described in U.S. Pat. No. 5,652,366, describing the isolation of rat adipocytes from epididymal Fat Pads. According to the method, adipose tissue is removed from anesthetized rats and rinsed twice in incubation medium (2.09 g sodium bicarbonate and 0.04 g EDTA, disodium salt, in 1 L Krebs buffer). Each rat (300–350 g) yields approximately 4 ml of adipose tissue. The adipose tissue (35 ml) is cut into small pieces with scissors and washed with incubation medium (50 ml). The mixture is poured into the barrel of a 50 ml syringe to which is attached a short piece of clamped tubing instead of a needle. The aqueous phase is allowed to drain. A second wash with incubation medium is passed through the syringe. The tissue is added to 50 ml of collagenase solution (collagenase (90 mg), bovine serum albumin (BSA) (500 mg), and 0.1 M calcium chloride solution (1 ml), in incubation medium (50 ml)) in a 1 L bottle. The mixture is shaken in an environmental at 37° C. for about 60 minutes under an atmosphere of 95% oxygen/5% carbon dioxide to effect digestion of the tissue. The dispersed cells are poured through 2 layers of cheese cloth into a 100 ml plastic beaker. The undigested clumps in the cloth are rinsed once with incubation medium (20 ml). The cells in the beaker are centrifuged in 2 plastic tubes for 30 seconds at room temperature at 300 rpm. The aqueous phase is aspirated from beneath the loosely packed layer of floating fat cells and discarded. The adipocytes are gently poured into a 250 ml plastic beaker containing 100 ml of rinse solution (1 g BSA per 100 ml incubation medium). After gentle stirring the centrifugation step is repeated. Another wash with rinse solution follows. The cells are pooled and their volume is estimated with a graduated cylinder. The adipocytes are diluted in twice their volume of assay buffer (incubation medium (120 ml), BSA (1.2 g), pyruvic acid (13 mg)).

An in vitro lipolysis assay using these freshly isolated adipocytes can be conducted as follows (as described in U.S. Pat. No. 5,652,366). The assay is performed in 20 ml plastic scintillation vials and the total assay volume is 4.2 ml. Assay buffer (2.5 ml), diluted adipocytes (1.5 ml), and a solution of the compound to be tested (12.3 mu L) adenosine agonist (12.3 mul; varying concentration) is incubated in the environmental shaker for 15 minutes, then the reaction is started with norepinephrine solution (41.2 mu L) (10 nM, in a carrier solution containing water (100 ml), BSA (4 mg), and 0.1 M EDTA (20 I. LL)) and adenosine deaminase (1 mu g/ml, 41.2 mu 1). After sixty minutes in the shaker the reaction is terminated by putting the vials on ice. The contents of each vial is transferred into a 12×75 mm glass tube and centrifuged at 8°–10° C. at 3600 rpm for 20 min. The hard lipid layer is removed by aspiration and the aqueous layer is assayed for glycerol (400 mu l of sample).

7. Exemplary Methods of the Invention for Treating and Preventing Diseases

The invention is based at least in part on the discovery that the JNK and the ERK/MAP kinase pathways are involved in TNF-α induced lipolysis, and that inhibition of these kinase pathways decreases or inhibits TNF-α induced lipolysis. It has also been shown that PPAR-γagonists inhibit TNF-α induced lipolysis. Thus, the invention pertains to any disease or disorder which is associated with, i.e., caused by or contributed to by, lipolysis, e.g., in adipocytes, such as TNF-α induced lipolyis. Furthermore, since lipolyis results in the release of free fatty acids (FFA) and glycerol, the invention pertains more generally to methods for treating diseases relating to an increase in free fatty acids and/or glycerol.

Increased circulating FFA have been demonstrated to have in particular the following actions: (i) it promotes or causes insulin resistance at the level of insulin-mediated glucose uptake in skeletal muscle. The defect seen is the same as the defect observed in obese individuals and type II diabetics; (ii) it increases hepatic gluconeogenesis, which results in increased glucose secreted into the blood. Type II diabetes is associated with fasting hyperglycemia—which is probably in part due to increased hepatic glucoeneogenesis; (iv) it increases insulin secretion initially and chronically. Evidence has suggested that this results in a decreased ability of the islet to secrete appropriate amounts of insulin for blood glucose-promoting type II diabetes; (v) it increases the liver's output of triglyceride associated lipoproteins resulting in hyperlipoproteinemia; (vi) it affects vascular tone possibly promoting hypertension; and (vii) it may also affect PAI-I-risk for thrombotic events such as stroke and myocardial infarction. Thus, all of these effects induced by increased circulating FFA can be treated according to the methods of the invention.

In a preferred embodiment, the invention provides methods for treating insulin resistance, i.e., a subnormal biological response to insulin, and diseases or conditions resulting therefrom or associated therewith. In fact, it has been shown that elevated blood levels of FFAs inhibit insulin-stimulated glucose uptake, i.e., induce insulin resistance, in healthy subjects and also in obese individuals and in patients with NIDDM (Boden and Chen (1995) *J. Clin. Invest.* 96:1261); Boden G. (1997) *Diabetes* 46:3). There is also strong evidence that in normal as well as in diabetic subjects, physiological elevations of plasma FFA levels lower peripheral insulin sensitivity dose-dependently.

Elevated FFA levels result at least in part from excessive lipolysis. In fact, it has been shown that excessive lipolysis is characteristic of NIDDM and possibly contributes to insulin resistance and hyperglycemia (Swislocki, A. L., *Horm. Metab. Res.* 1993 (25), 90–95). Similarly, excessive fat accumulation, such as seen in obesity, is associated with elevated plasma FFA levels. Thus, increased FFA plasma levels are produced at least in part by an increase in rate of lipolysis from an expanded fat cell mass (Jensen et al. (1989) *J. Clin. Invest.* 83:1168). Accordingly, insulin resistance can result from an increase in lipolysis.

Frequently, an excessive lipolysis results from an increase in TNF-α. In fact, TNF-α has been shown to increase lipolysis (see, e.g., Examples herein). Furthermore, as shown herein, there is a direct correlation between the amount of TNF-α in serum and the percentage of body fat in humans (see Example 10). In addition, it has been observed that TNF-α is overexpressed in the adipose tissue of obese insulin-resistant rodents and humans and that the neutralization of TNF-α in fa/fa Zucker rats resulted in a decreased level of plasma FFA, decreased insulin resistance, and increased insulin-receptor tyrosine kinase activity in adipose tissue and muscle (Hotamisligil and Spiegelman (1994) *Diabetes* 43:1271). Furthermore, infusion of TNF-α in humans increased plasma FFAs (Van der Poll et al., (1991) *Am J. Physiol.* 24:E457). Thus, insulin resistance and conditions resulting therefrom can result from increased plasma FFA levels caused by increased lipolysis, and in particular from increased TNF-α induced lipolysis. Accordingly, by providing a method for reducing lipolysis, the invention provides therapeutic methods for treating diseases or conditions resulting form excessive lipolysis and elevated plasma FFA levels, such as insulin resistance and conditions deriving therefrom. For example, insulin resistance can be treated by administration to a subject of a compound which inihibits TNF-α biological function, by, e.g., inhibiting TNF-α production or TNF-α action on cells, such as with inhibitors of ERK/MAP kinase and/or JNK signalling pathway.

A consequence of the resistance is that glucose concentrations rise. This leads, in turn, to an increased release of insulin. Hyperinsulinemia, both in the fasting and postprandial states, is a hallmark of insulin resistance. Hyperinsulinemia is also caused by stimulation of gluconeogenesis, which in turn is caused by elevated FFA levels. Thus, high plasma FFA levels induce elevated plasma levels of insulin, for compensating the FFA induced insulin resistance and FFA stimulation of gluconeogenesis. Epidermilogical studies have shown that hyperinsulinemia is a risk factor for morbidity and mortality in cardiovascular disease (Smith U. (1994) *Am. J. Clin. Nutr.* 59, suppl. 686S). Accordingly, the invention also provides therapeutics and methods for reducing or preventing hypersecretion of insulin and disorders or conditions resulting therefrom.

Insulin resistance is associated with, or contributes to, NIDDM. Accordingly, in a preferred embodiment, the invention provides a method for treating or preventing NIDDM in a subject and complications of NIDDM, by preventing or inhibiting excessive plasma FFA levels. NIDDM can be defined as a state in which a normal amount of insulin produces a subnormal biologic response. This is a condition in which available insulin, secreted by the pancreas and circulating in the bloodstream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose. In insulin-treated patients with diabetes, insulin resistance is considered to be present whenever the therapeutic dose of insulin exceeds the secretory rate of insulin in normal persons.

NIDDM is associated with various complications. As defined herein, "complications of NIDDM" is referred to as cardiovascular complications or several of the metabolic and circulatory disturbances that are associated with hyperglycemia, e.g., insulin resistance, hyperinsulinemia and/or hyperproinsulinemia, delayed insulin release, dyslipidemia, retinopathy, peripheral neuropathy, nephropathy, hypertension, and other coronary artery diseases (CADs). CAD is a major cause of morbidity and mortality in patients with NIDDM. Thus, by providing therapeutics and methods for reducing lipolysis and excessive FFA levels, the invention provides therapeutics and methods for treating and preventing NIDDM and consequences thereof.

The invention also provides therapeutics and methods for treating and preventing having impaired glucose tolerance (IGT). The usual meaning of impaired glucose tolerance is that it is a condition associated with insulin-resistance which is intermediate between frank, NIDDM and normal glucose tolerance (NGT). A high percentage of the IGT population is known to progress to NIDDM relative to persons with normal glucose tolerance (Saad, et al., *New Engl J Med* 1988; 319:1500–6). Thus, by providing therapeutics and methods for reducing or preventing IGT, i.e., for normalizing insulin resistance, the progression to NIDDM can be delayed or prevented.

IGT is diagnosed by a procedure wherein an affected person's postprandial glucose response is determined to be abnormal as assessed by 2-hour postprandial plasma glucose levels. In this test, a measured amount of glucose is given to the patient and blood glucose levels measured regular intervals, usually every half hour for the first two hours and every hour thereafter. In a "normal" or non-IGT individual glucose levels rise during the first two hours to level less than 140 mg/dl and then drop rapidly. In an IGT individual, the blood glucose levels are higher and the drop-off level is at a slower rate.

Resistance to insulin-stimulated glucose uptake in individuals who do not become frankly hyperglycemic nevertheless increases the likelyhood of these individuals to develop numerous other diseases. In particular, an attempt to compensate for insulin resistance sets in motion a series of events that play an important role in the development of both hypertension and coronary artery disease (CAD), such as premature atherosclerotic vascular disease. This cluster of abnormalities is commonly called the "Metabolic Syndrome", or the "Insulin-Resistance Syndrome" or "Syndrome X". Metablic syndrome includes usually obesity, insulin resistance, hypertension, hyperlipidemia, increased risk of developing type II diabetes, atherosclerotic disease including stroke and myocardial infarction. Increased plasma triglyceride and decreased HDL-cholesterol concentrations, conditions which are known to be associated with CAD, have also been reported to be associated with insulin resistance. Thus, by providing therapeutics and methods for reducing or preventing insulin resistance, the invention provides methods for reducing and/or preventing the appearance of insulin-resistance syndrome.

Yet other diseases are associated with insulin resistance and, thus, be treated or prevented according to the methods of the invention. For example, obesity, which is the result of an imbalance between caloric intake and energy expenditure is highly correlated with insulin resistance and diabetes (Hotamisligil, Spiegelman et al., Science, 1993, 259:87–91). In humans obesity can be defined as a body weight exceeding 20% of the desirable body weight for individuals of the sane sex, height and frame (Salans, L. B., in *Endocrinology & Metabolism,* 2d Ed., McGraw-Hill, New York 1987, pp. 1203–1244; see also, R. H. Williams, *Textbook of Endocrinology,* 1974, pp. 904–916). In other animals (or also in humans) obesity can be determined by body weight patterns correlated with prolactin profiles given that members of a species that are young, lean and "healthy" (i.e., free of any disorders, not just metabolic disorders) have daily plasma prolactin level profiles that follow a regular pattern that is highly reproducible with a small standard deviation. Obesity, or excess fat deposits, correlate with and may trigger the onset of various lipid metabolism disorders, e.g. hypertension, Type II diabetes (NIDDM), atherosclerosis, cardiovascular disease, etc. Even in the absence of clinical obesity (according to the above definition) the reduction of body fat stores (notably visceral fat stores) in man especially on a long-term or permanent basis would be of significant benefit, both cosmetically and physiologically. Thus, by preventing or treating obesity, the methods of the invention will allow an individual to have a more comfortable life and avoid the onset of various diseases triggered by obesity.

In particular, a risk factor for obesity/NIDDM related cardiovascular disease may be elevated levels of plasminogen activator inhibitor-1 (PAI-1). It has recently been shown that increased PAI-1 originates primarily from the adipocyte in response to chronically elevated levels of TNF-α, insulin and transforming growth factor-beta (TGF-β) (Samad et al., (1997) *J. Clin. Invest.* 97:37). Thus, treatment of a subject, e.g., an obese subject or a subject having NIDDM, according to the method of the invention, such as by administration of a compound inhibiting TNF-α action, can prevent cardiovascular disease.

Furthermore, the methods of the invention can also be used to generally prevent or treat cardiovascular diseases such as atherosclerosis, in addition to those caused by obesity and/or NIDDM. In fact, it is likely that at least a significant percentage of cardiovascular diseases are caused by or contributed to by an abnormal level of TNF-α, such as TNF-α secreted by cells, e.g., monocytic cells, during an inflammatory reaction. Thus, by inhibiting the production and/or action of TNF-α, one can reduce the likelyhood of developing or reduce cardiovascular diseases.

In yet another embodiment, the invention provides a method for treating a subject having polycystic ovary syndrome (PCOS). PCOS is among the most common disorders of premenopausal women, affecting 5–10% of this population. It is a syndrome of unknown etiology characterized by hyperandrogenism, chronic anovulation, defects in insulin action, insulin secretion, ovarian steroidogenesis and fibrinolysis. Women with PCOS frequently are insulin resistant and at increased risk to develop glucose intolerance or NIDDM in the third and fourth decades of life (Dunaif et al. (1996) *J. Clin. Endocrinol. Metab.* 81:3299). Hyperandrogenism also is a feature of a variety of diverse insulin-resistant states, from the type A syndrome, through leprechaunism and lipoatrophic diabetes, to the type B syndrome, when these conditions occur in premenopausal women. It has been suggested that hyperinsulinemia per se causes hyperandrogenism. Insulin-sensitizing agents, e.g., troglitazone, have been shown to be effective in PCOS and that, in particular, the defects in insulin action, insulin secretion, ovarian steroidogenosis and fibrinolysis are improved (Ehrman et al. (1997) *J. Clin. Endocrinol. Metabolism* 82:2108). Based at least on the fact that the method of the invention are useful for treating insulin-resistant states, the instant method can be used for treating PCOS.

Elevated circulating FFA levels has also been shown to impair endothelial function, in particular endothelium-dependent vasodilation (Steinberg et al. (1997) *J. Clin. Invest.* 100:1230), such as in insulin-resistant humans. Accordingly, the invention provides methods for normalizing endothelial function.

Insulin resistance is also often associated with infections and cancer. Thus, prevention or reducing insulin resistance according to the methods of the invention may prevent or reduce infections and cancer.

Insulin resistance can be diagnosed by various methods, such as by the intravenous glucose tolerance test or by measuring the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. Another way to do this is to follow the approach as disclosed in The New England Journal of Medicine, No. 3, pp. 1188 (1994), i.e. to select obese subjects as an initial criteria for entry into the treatment group. Some obese subjects have impaired glucose tolerance (IGT) while others have normal glucose tolerance (NGT). Since essentially all obese subjects are insulin resistant, i.e. even the NGT obese subjects are insulin resistant, they have fasting hyperinsulinemia. Therefore, the target of the treatment according to the present invention can be defined as NGT individuals who are obese or who have fasting hyperinsulinemia, or who have both.

Insulin resistance can also be diagnosed by the euglycemic glucose clamp test. This test involves the simultaneous administration of a constant insulin infusion and a variable rate glucose infusion. During the test, which lasts 3–4 hours, the plasma glucose concentration is kept constant at euglycemic levels by measuring the glucose level every 5–10 minutes and then adjusting the variable rate glucose infusion to keep the plasma glucose level unchanged. Under these circumstances, the rate of glucose entry into the bloodstream is equal to the overall rate of glucose disposal in the body. The difference between the rate of glucose disposal in the basal state (no insulin infusion) and the insulin infused state, represents insulin mediated glucose uptake. In normal individuals, insulin causes brisk and large increase in overall body glucose disposal, whereas in NIDDM subjects, this effect of insulin is greatly blunted, and is only 20–30% of normal. In insulin resistant subjects with either IGT or NGT, the rate of insulin stimulated glucose disposal is about half way between normal and NIDDM. For example, at a steady state plasma insulin concentration of about 100 uU/ml (a physiologic level) the glucose disposal rate in normal subjects is about 7 mg/kg/min. In NIDDM subjects, it is about 2.5 mg/kg/min, and in patients with IGT (or insulin resistant subjects with NGT) it s about 4–5 mg/kg/min. This is a highly reproducible and precise test, and can distinguish patients within these categories. It is also known, that as subjects become more insulin resistant, the fasting insulin level rises. There is an excellent positive correlation between the height of the fasting insulin level and the magnitude of the insulin resistance as measured by euglycemic glucose clamp tests and, therefore, this provide the rationale for using fasting insulin levels as a surrogate measure of insulin resistance.

Thus, any of the above-described tests or other tests known in the art can be used to determine that a subject is insulin-resistant, which patient can then be treated according to the methods of the invention to reduce or cure the insulin-resistance. Alternatively, the methods of the invention can also be used to prevent the development of insulin resistance in a subject, e.g., those known to have an increased risk of developing insulin-resistance.

In a particular embodiment, insulin resistance or other disease or condition associated with an abnormal FFA level is reduced, eliminated or inhibited, by blocking TNF-α action, e.g., by neutralizing TNF-α in the serum (i.e., circulating TNF-α) or in the adipose tissue. Alternatively, insulin resistance can be treated with agents which inhibit the production of TNF-α from cells, e.g., adipocytes, but also from other types of cells such as macrophages. In yet another embodiment, the action of TNF-α is inhibited by treatment with agents which interfere with the signal transduction pathway induced by binding of TNF-α to its receptor. Such inhibitors include compounds which inhibit the ERK/MAP kinase and/or JNK signaling pathway. In an illustrative embodiment, NIDDM is treated or inhibited by administrating to a subject in need a pharmaceutical composition comprising a compound which inhibit TNF-α biological activity.

8. Formulations and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insulation (either through the mouth or the nose) or oral, buccal, parenteral or rectal administration.

In certain embodiments, the therapy is conducted by gene therapy, e.g., by admininstering to a subject in need thereof a pharmaceutically effective amount of an expression vector encoding a protein or an RNA which inhibits or at least reduces the activity of an enzyme in the MAP kinase and/or JNK pathway. In one embodiment, the protein is a dominant negative mutant of an enzyme, e.g., a dominant negative mutant of ERK-1 or ERK-2 or JNK. The protein can also be an intracellular antibody, e.g., a single chain antibody. In yet other embodiments, the expression vector encodes antisense RNA.

In a preferred embodiment, the nucleic acid encoding the protein or RNA is operably linked to all necessary transcriptional and translational regulatory elements, such as a promoter, enhancer and polyadenylation sequence. Regulatory sequences are art-recognized and are described, e.g., in Goeddel; Gene Expression Technology: Methods in Enzymology 185, Academic Press, San Diego, Calif. (1990). In a preferred embodiment, the promoter is a constitutive promoter, e.g., a strong vi promoter, e.g., CMV promoter. The promoter can also be cell- or tissue-specific, that permits substantial transcription of the DNA only in predetermined cells, e.g., adipocytes. Exemplary adipocyte specific promoters include the leptin and the aP2 gene promoters, described, e.g., in Hollenberg et al. *J Biol Chem* (1997); 272:5283, as well as the hormone sensitive lipase gene promoter, described, e.g., in Grober et al. *Biochem J* (1997) 328: 453. The promoter can also be an inducible promoter, e.g., a metallothionein promoter. Other inducible promoters include those that are controlled by the inducible binding, or activation, of a transcription factor, e.g., as described in U.S. Pat. Nos. 5,869,337 and 5,830,462 by Crabtree et al., describing small molecule inducible gene expression (a genetic switch); International patent applications PCT/US94101617, PCT/US95/10591, PCT/US96/09948 and the like, as well as in other heterologous transcription systems such as those involving tetracyclin-based regulation reported by Bujard et al., generally referred to as an allosteric "off-switch" described by Gossen and Bujard (Proc. Natl. Acad. Sci. U.S.A. (1992) 89:5547) and in U.S. Pat. Nos. 5,464,758; 5,650,298; and 5,589,362 by Bujard et al. Other inducible transcription systems involve steroid or other hormone-based regulation.

The nucleic acid encoding the RNA or protein of interest and optionally regulatory elements may be present in a plasmid or a vector, e.g., an expression vector. Any means for the introduction of these polynucleotides into mammals, human or non-human, may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA construct may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal. See, e.g., Canonico et al, Am J Respir Cell Mol Biol 10:24–29, 1994; Tsan et al Am J Physiol 268; Alton et al., Nat Genet 5:135–142, 1993 and U.S. Pat. No. 5,679,647 by Carson et al. Colloidal dispersion systems.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject.

In a preferred method of the invention, the DNA constructs are delivered using viral vectors. The transgene may be incorporated into any of a variety of viral vectors useful in gene therapy, such as recombinant retroviruses, adenovirus, adeno-associated virus (AAV), and herpes simplex virus-1, or recombinant bacterial or eukaryotic plasmids. While various viral vectors may be used in the practice of this invention, AAV- and adenovirus-based approaches are of particular interest Such vectors are generally understood to be the recombinant gene delivery system of choice for the transfer of exogenous genes in vivo, particularly into humans. Viral vectors are abundantly described in the art and are available from the American Type Culture Collection, Rockville, Md., or by request from a number of commercial and academic sources.

The expression constructs and therapeutics of the invention can be tested out in animals. In particular, animal models for insulin resistant diseases or FFA-related disorders are available. For example, a frequently used animal model for insulin resistance is the streptozotocin diabetic mouse, which is described, e.g., in Tozzo et al. *Endocrinology* (1997); 138:1604. This article describes the use of this animal model for improving insulin resistance by overexpression of GLUT4 driven by an adipose-specific promoter. Other animal models include the fa/fa Zucker rats described herein. Diabetic Ksj db/db mice and spontaneously hypertensive rats (SHR) are described, e.g., in Wasner et al. *Acta Diabetol* 1997; 34:257. Another model that is frequently used is the ob/ob mouse, a model of the insulin resistance of obesity and non-insulin-dependent diabetes mellitus, which is described, e.g., in Kerouz et al. *J Clin Invest* 1997;100:3164.

The compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for a therapeutic gene of interest, e.g., a gene encoding a ribozyme or an antisense molecue, can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). A gene of interest can be delivered in a gene therapy construct by electroporation using techniques described, for example, by Dev et al. ((1994) *Cancer Treat Rev* 20:105–115).

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

9. Diagnostic Methods of the Invention

The invention further provides diagnostic methods for determining whether a subject has or is likely to develop a condition associated with excessive lipolysis, e.g., TNF-induced lipolysis, and/or elevated plasma FFA level. In one embodiment, the diagnostic method comprises determining whether a MAP kinase, e.g., ERK1/2 and JNK, activity is normal. In fact, since inhibition of TNF-α induced lipolysis is associated with inhibition of the ERK1/2 and of the JNK pathway, it is believed that increased activity of ERK1/2 and/or of the JNK pathway, and in particular increased activity of JNK-1 can result in increased lipolysis and release of FFA. Thus, by determining the level of activity of a MAP kinase, e.g., ERK1/2 and JNK-1, in cells of a subject, it is possible to predict whether the subject has or is likely to develop a condition associated with excessive lipolysis, e.g., insulin resistance and consequences thereof.

Determining the level of activity of a MAP kinase, e.g., ERK1/2 and JNK-1, can be performed by any of numerous methods known in the art. In one embodiment, the activity of the MAP kinase is determined by determining the amount of MAP kinase or mRNA in a cell of the subject. Measuring the level of mRNA can be done, e.g., by Northern blot hybridization, reverse transcription-polymerase chain reaction (RT-PCR), or in situ hybridization. Measuring the level of protein can be done by immunoprecipitation and/or Western blot or by immunohistochemistry. Antibodies are available commercially, or can be prepared as described herein Alternatively, the state of phosphorylation of the MAP kinase can be determined, e.g,. by using antibodies which specifically recognize the phosphorylated form of the protein. Alternatively, the kinase activity of MAP kinase is determined. This can be done, e.g., as described in the Examples.

In another embodiment, the diagnostic method comprises determining whether the MAP kinase gene, e.g., gene encoding an ERK or JNK protein, comprises a mutation. Techniques for determining the presence of a mutation in a gene may comprise sequencing the gene or portion thereof, allele specific hybridization, allele specific amplification, single strand conformation polymorphism (SSCP) analysis and other techniques known in the art. A potential mutation is likely to be located in a region of the gene affecting either transcription, translation, splicing, stability of the gene or the amino acid sequence of the protein encoded by the gene.

In other embodiments, the diagnostic methods of the invention comprise determining the activity of a PPAR-γ receptor. In fact, since binding of a ligand to a PPAR-γ receptor inhibits TNF-α induced lipolysis, a defective PPAR-γ may result in increased TNF-α nduced lipolysis. Determining the activity of a PPAR-γ receptor may comprise determining the level of expression of the receptor, or the binding affinity of a ligand to the receptor. Alternatively, it may comprise determining the level of signal transduction from the receptor or determining whether the gene encoding PPAR-γ comprises a mutation.

The invention also provides a method for determining the percentage body fat of an individual. As set forth in the Examples, it has been shown that there is a direct correlation between the level of serum TNF-α, as well as IL-6 and leptin, and the percentage body fat of an individual (see, e.g., FIG. 11). Accordingly, in a preferred embodiment, the invention comprises determining the serum level of a cytokine in a subject and comparing this level to a reference table or graph representing the serum cytokine level and percentage body fat of a representative number of individuals, to thereby derive the individual's percentage body fat. In an even more preferred embodiment, the cytokine is TNF-α. In another embodiment, the cytokine is IL-6. Yet in another embodiment, the serum level of a hormone, such as leptin is determined. The method of the invention is advantageous over classic methods for determining the percentage of body fat of an individual at least because it is much easier to carry out.

Figure 11A:
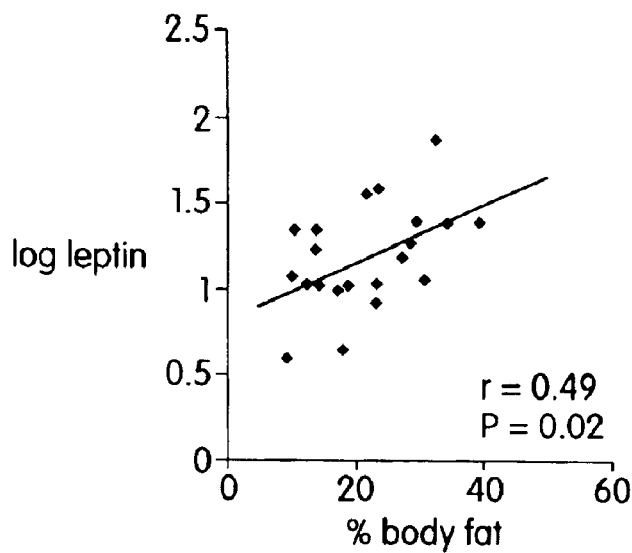
FIG. 11A is a graph representing the logarithm of the value of circulating leptin as a function of the percentage body fat of an individual.
Figure 11B:
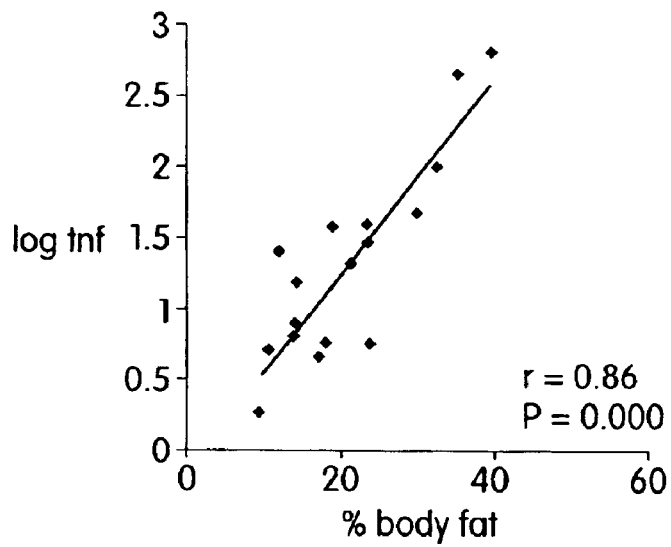
FIG. 11B is a graph representing the logarithm of the value of circulating TNF-α as a function of the percentage body fat of an individual.
Figure 11C:
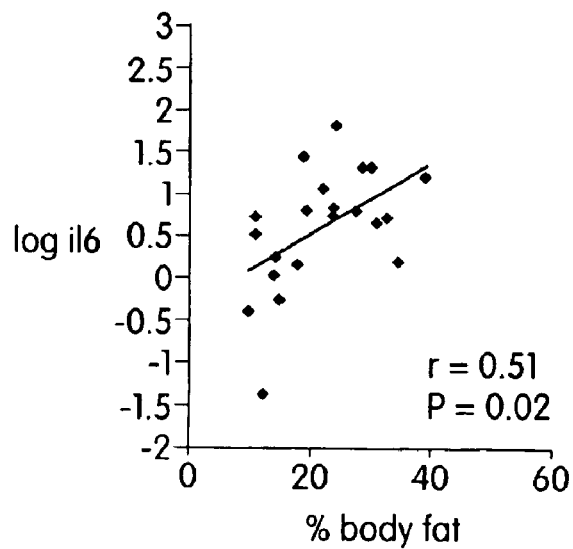
FIG. 11C is a graph representing the logarithm of the value of circulating leptin IL-6 as a function of the percentage body fat of an individual.

The reference table or graph can comprise data from any individual. Alternatively, the reference table or graph comprises the data from a certain group of individuals, such as women, males, normal or healthy individuals, obese individuals, insulin-resistant individuals, hyper- or hypo-insulinemic individuals or individuals having diabetes, e.g., NIDDM. Examples of graphs are represented in FIG. 11. The serum level of the cytokine TNF-α in the graphs is preferably indicated in the logarithmic form, as shown in FIG. 11. Such reference graphs and tables are withing the scope of the invention, as well as methods for establishing them.

The serum level of a cytokine, e.g., TNF-α or IL-6, or of a hormone, e.g., leptin, in a subject can be determined by a variety of methods known in the art, such as assays using reagents, e.g., antibodies, interacting specifically with the cytokine or hormone. A preferred method of detection is by performing ELISA assays. An ELISA assay for the detection of human TNF-α, as well as the production of antibodies against human TNF-α, is described, e.g., in U.S. Pat. No. 5,716,972 by Adams et al. Antibodies for performing these assays are also commercially available, such as from Sigma Chemical Co. St. Louis, Mo. Antibodies can also be prepared as further described herein.

10. Kits

In one embodiment, the invention provides a therapeutic kit. In a exemplary embodiment, the therapeutic kit comprises at least one inhibitor of ERK1/2 and/or of the JNK pathway in a pharmaceutically acceptable carrier and instructions for use. The kit can further comprise another inhibitor of the MAPK/ERK pathway. The inhibitor can be a nucleic acid, e.g., an antisense DNA or RNA, a protein, a ribozyme, a triplex molecule, or a small molecule. The kit can also comprise an agonist of a PPAR-γ receptor.

In another embodiment, the invention provides a diagnostic kit. The kit can comprise, e.g., a probe or an antibody for detecting mRNA, DNA, or protein of interest. For example, the kit can comprise a probe that is capable of specifically recognizing ERK1/2 or JNK-1 DNA or RNA. The kit can also comprise reagents necessary for determining the kinase activity of a kinase in the ERK1/2 and/or the JNK pathway, e.g., JNK-1. In other embodiments, the kits can comprise reagents for determining the activity of a PPAR-γ receptor, e.g., a probe detecting PPAR-γ receptor nucleic acid.

In yet another embodiment, the invention provides a kit for determining the percentage body fat of a subject. In a preferred embodiment, the kit comprises at least one reagent for determining the serum level of a cytokine, such as TNF-α or IL-6, or the serum level of a hormone, such as leptin. In an even more preferred embodiment, the kit comprises at least one anti-TNF-α or IL-6 or leptin antibody. The kit preferably further comprises a reference table or graph representing the serum level of a cytokine or hormone and the percentage body fat of a representative number of individuals. This reference table or graph can be used to determine the percentage of body fat of a subject by comparing the serum level of a cytokine or a hormone of the individual with the data represented in the table or graph. In addition the kit can comprise one or more reagent for determining the level of cytokine or hormone in the serum and/or a utensil for obtaining and/or storing serum from a subject. The kit may also comprise instructions for use.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2$^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Sodium Salicylate and the PPAR-γ Agonists BRL and PGJ2 each Block TNF-α Induced Lipolysis This example demonstrates that salicylic acid, as well as the PPAR-γ agonists BRL and PGJ2 are capable of blocking TNF-α induced lipolysis.

3T3-L1 adipocytes used in this example were obtained from 3T3-L1 fibroblasts as follows. 3T3-L1 fibroblasts (ATCC Deposit NO. CL-173, described in U.S. Pat. No. 4,003,789) were cultured in Dulbecco's Modified Eagle's Medium (DMEM) containing 10% bovine calf serum, and induced to differentiate into adipocytes using standard protocols, as described, e.g., in Kohanski et al. (1996) *J. Biol. Chem.* 261:12272. Adipocytes were used 10–15 days after the differentiation protocol was initiated.

Differentiated 3T3-L1 adipocytes cultured in 12 well plates were incubated overnight in DMEM+0.5% BSA in the absence of serum. The following morning, the cells were incubated in the presence or absence of 2 mM or 20 mM sodium salicylate (NaSal) and treated with recombinant murine TNF-α (m TNF-α; Genzyme; Cambridge, Mass.) with or without 17 μM 15-deoxy-$^{12,14}$-PGJ2 ("PGJ2"; Cayman Chemical; Ann Arbor, Mich.) or 10 μM BRL 49653 ("BRL"; Smith Kine Beecham (Hamish Ross) (King of Prussia, Pa.)) for 24 hours. The glycerol content in the culture medium was determined using a colorimetric assay (GPO-Trinder, Sigma, St Louis, Mich.). Protein content was determined using the BCA (bicinchonic acid) protein assay (Pierce, Rockford, Ill.). The results are indicated as nmol glycerol per mg protein.

Figures 1, 4A:
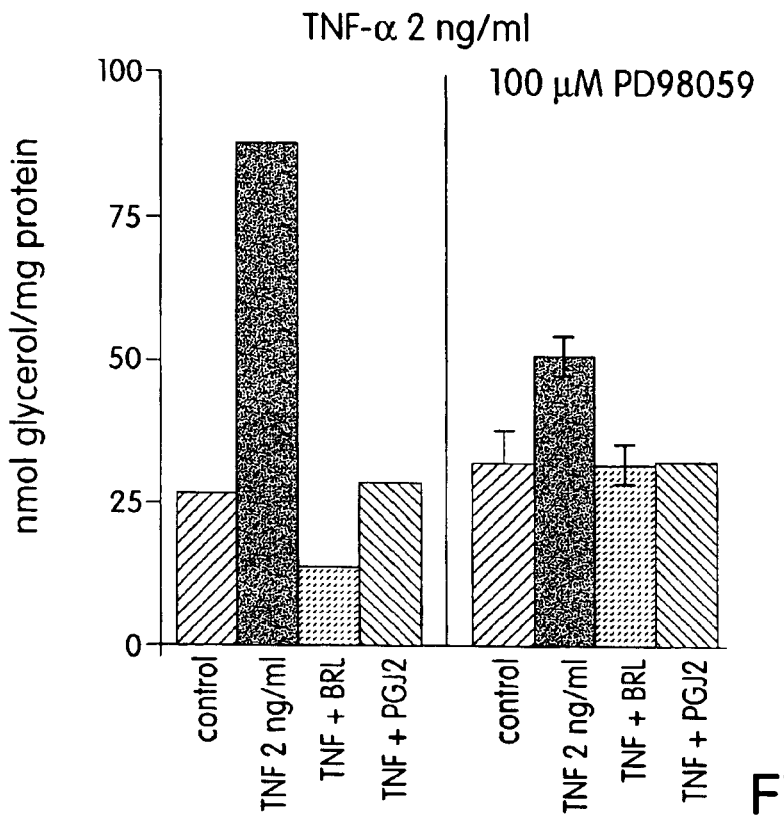
FIG. 4A shows the amount of glycerol produced from 3T3-L1 adipocytes treated for 24 hours with or without 2 ng/ml THF-α (Panel A), 10 ng/ml TNF-α (Panel B), BRL, PGJ2 and 100 μM PD98059.

The results are shown in FIG. 1. These indicate that lipolysis in the adipocytes induced by 2 ng/ml (Panel A) or 20 ng/ml (Panel B) TNF-α is significantly inhibited by the addition of 2 or 20 mM NaSal. In fact, NaSal inhibited glycerol production by 3T3-L1 adipocytes induced by 2 ng/ml TNF-α by a factor of 3–4. Furthermore, as little as 2 mM NaSal inhibited glycerol production induced by 10 ng/ml TNF-α by about a factor 2.

Lipolysis induced by TNF-α was also significantly inhibited by the PPAR-γ2 agonists BRL and PGJ2. This effect was much stronger at a dose of TNF-α of 2 ng/ml as opposed to 10 ng/ml. The addition of BRL or PGJ2 to cells incubated with 20 mM NaSal did not further reduce lipolysis compared with cells incubated with 26 mM NaSal alone. In the cell cultures incubated with only 2 mM NaSal, the addition of BRL or PGJ2 reduced glycerol production slightly (less than a factor 2).

Thus, 20 mM NaSal completely blocked the ability of TNF-α to increase lipolysis in adipocytes and as little as 2 mM NaSal partially reduced this process. Furthermore, BRL and PGJ2 also inhibit TNF-α induced lipolysis.

In another example, the protective effect of BRL concentration on TNF-α induced lipolysis was analyzed.

Accordingly, 3T3-L1 adipocytes were treated with BRL at 10 μM, 1 μM or 1 nM and TNF-α as described above, and the amount of glycerol was determined after 24 hours. BRL treatment with 1 μM BRL was as effective as with 10 μM, whereas 1 nM was not effective at protecting the cells against lipolysis by TNF-α.

Figure 1C:
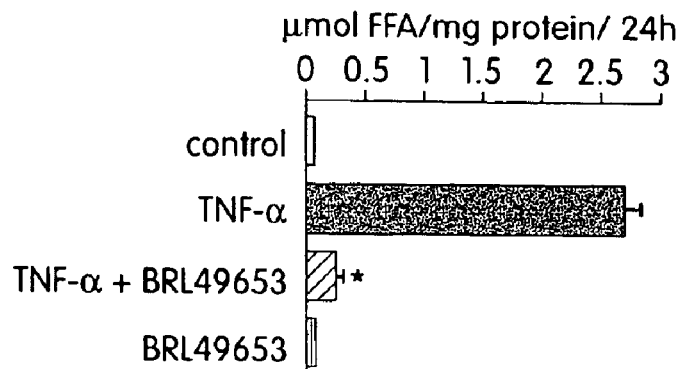
FIG. 1C shows the amount of free fatty acids (FFA) produced from 3T3-L1 adipocytes incubated for 24 hours in the presence or absence of 10 ng/ml TNF-α and BRL.

As indicated above, BRL reduced glycerol accumulation in TNF-α treated cells by about 58% compared to TNF-α treated cells. As shown in FIG. 1C, BRL also dramatically reduced TNF-α induced FFA release by about 90%, whereas BRL alone had no effect on FFA release. In this example, cells were treated for 24 hours as described above, and FFA levels in the culture medium were determined using a colorimetric kit (NEFA-C, WAKO Pure Chemicals, Osaka, Japan).

Figure 1D:
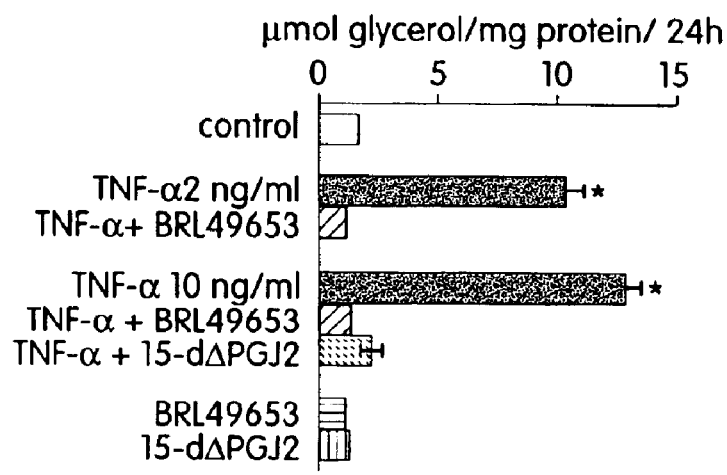
FIG. 1D shows the amount of glycerol produced from 3T3-L1 adipocytes during the last 24 hours of a 5 day incubation with or without TNF-α, BRL and PGJ2.

Prolonged treatment with PPAR-γ2 agonists showed an even more important blockage of glycerol release from TNF-α treated adipocytes. 3T3-L1 adipocytes were treated with TNF-α (2 or 10 ng/ml), TNF-α plus BRL at 10 μM, TNF-α plus PGJ2 at 15 μM, or BRL or PGJ2 alone for 5 days. The media was replaced everyday and collected on day 5 to measure accumulation of glycerol. As shown in FIG. 1D, prolonged treatment with 2 ng/ml of TNF-α resulted in an approximate 10 fold increase in glycerol accumulation during the last 24 hours of the 5-day treatment as compared with untreated controls, while 10 ng/ml of TNF-α caused an approximate 13 fold increase. Significantly, each of the PPAR-γ2 agonists blocked about 100% of the increase in glycerol release due to TNF-α treatment. Glycerol accumulation in adipocytes incubated with either BRL or PGJ2 alone was not different from levels measured in control (untreated) cells. Thus, prolonged treatment (5 days) with PPAR-γ2 agonists is more effective than a 24 hour treatment in blocking TNF-α induced glycerol release.

Figure 1E:
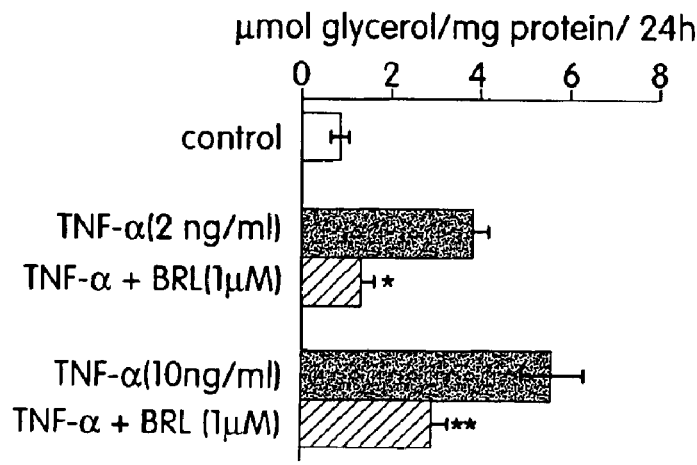
FIG. 1E shows the amount of glycerol produced from 3T3-L1 cells pretreated for 24 hours with TNF-α and then incubated with TNF-α alone or together with BRL.

To determine whether the PPAR-γ2 agonists were also effective in reducing lipolysis in cells that had been pretreated with TNF-α, 3T3-L1 adipocytes were incubated with 2 or 10 ng/ml of TNF-α for 24 hours, followed by another 24 hour incubation with TNF-α in the absence or presence of BRL (1 μM). As shown in FIG. 1E, BRL reduced the increase in glycerol release associated with TNF-α (2 or 10 ng/ml) by about 65% and about 50%, respectively. The earliest time point at which BRL began to reverse the effect of TNF-α on glycerol release was 6 hours after addtition of BRL. Thus, PPAR-γ2 agonists antagonized TNF-α-induced lipolysis when adipocytes were pretreated with TNF-α and when initially coincubated together. In contrast, neither BRL nor PGJ2 was able to block catecholamine (isoproterenol)-induced glycerol release, indicating that the mechanism of action of TNF-α and of catecholamines in inducing adipocyte lipolysis is different.

Accordingly, this example provides the first direct evidence that one of the mechanisms by which PPAR-γ2 agonists, such as TZDs, may increase systemic insulin sensitivity is by blocking TNF-α mediated FFA release from adipocytes.

Example 2

NaSal Inhibits TNF-α Induced JNK-1 Activation in Adipocytes

This example shows that NaSal inhibits JNK-1 activation by TNF-α in adipocytes.

3T3-L1 adipocytes were pretreated for 3 hours with or without 20 mM NaSal, with or without 100 μM MAP kinase kinase (MEK) inhibitor PD98059 (Biomol; Cat. No. EI-360) and then for 15 minutes with 10 ng/ml mTNF-α. JNK-1 kinase assays were then performed with extracts of each of these cell cultures on an N-terminal portion of c-jun, as described in Derjarde et al. (1994) Cell 76: 1025.

Figure 2:
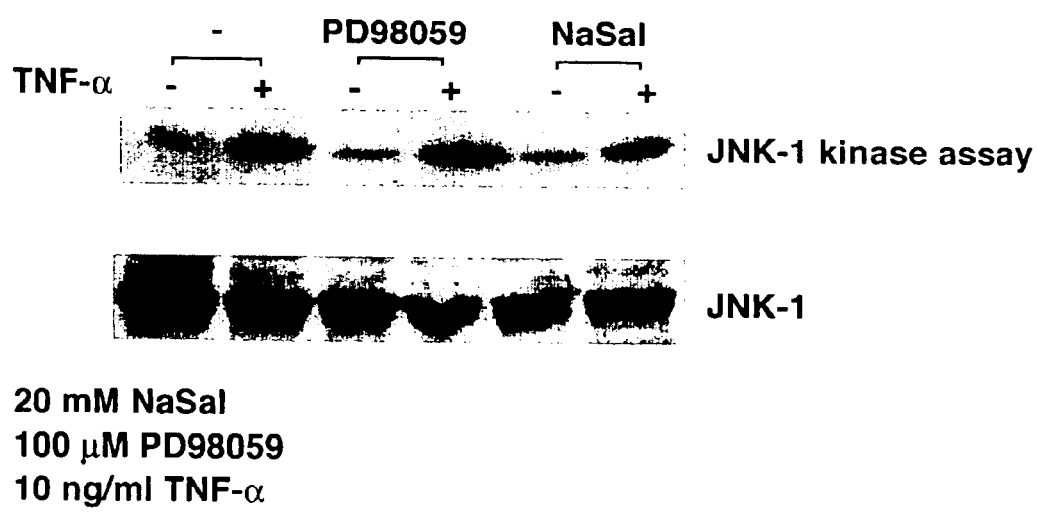
FIG. 2 represents a photograph of a Western blot showing (on the top line) the activity of JNK-1, as measured in a kinase assay, in 3T3-L1 adipocytes treated for 24 hours with or without 20 mM sodium salicylate (NaSal), 100 μM PD98059 and 10 ng/ml TNF-α and the total amount of JNK-1 as determined by Western blot analysis using a anti-JNK-1 antibody (bottom line).

The results are shown in FIG. 2. The results indicate that TNF-α induces activation of JNK-1 and this activation is significantly reduced by NaSal, but not by the MAK kinase inhibitor PD98059.

Thus, since NaSal inhibits TNF-α induced lipolysis and NaSal significantly reduces JNK-1 activation, JNK-1 activation is likely to play a significant role in blocking lipolysis induced by TNF-α.

Example 3

NaSal Partially Inhibits TNF-α Induced MAP Kinase Activation

This example shows that, similarly to JNK-1 activation by TNF-α, activation of MAP kinases by TNF-α is also inihibited by NaSal.

In this example, 3T3-L1 cells were treated as described in Example 2, and cell extracts were used in an ERK 1/2 kinase assay, using MBP (myelin basic protein) as a substrate. The assay used is described in Boulton et al. (1991) Cell Reg. 2: 357.

Figure 3:
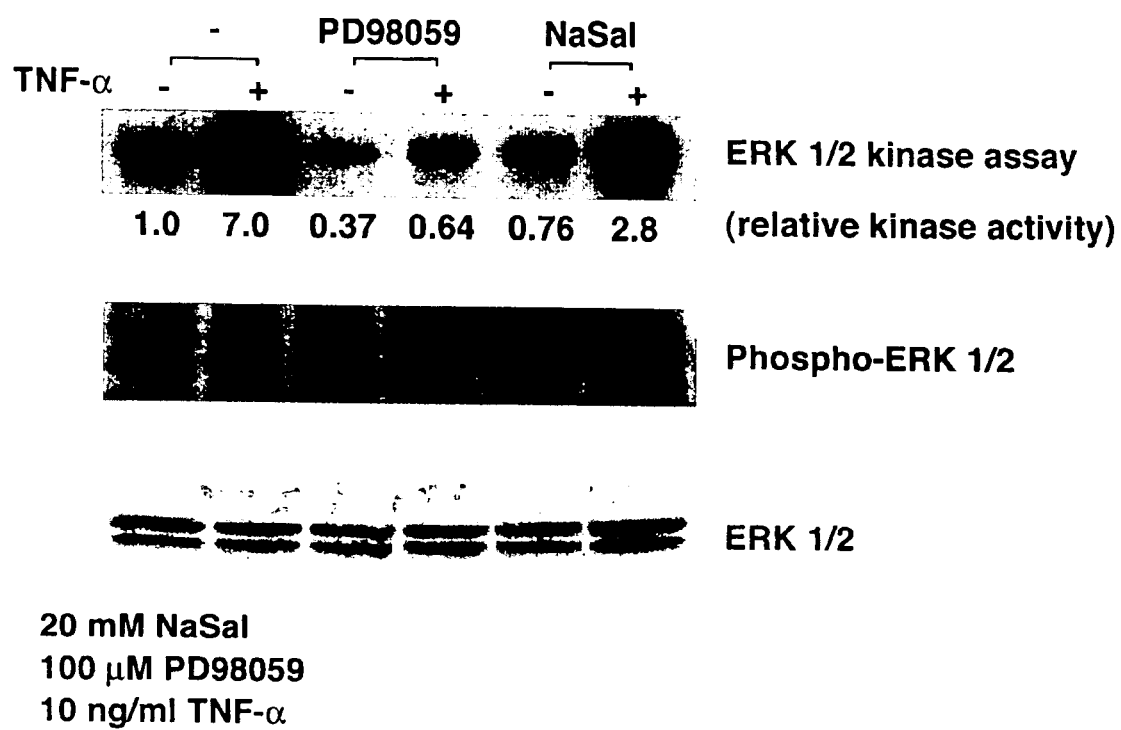
FIG. 3 represents a photograph of a Western blot showing the kinase activity of ERK1/2 (top line) and the the level of phosphorylated ERK1/2 (middle line) in 3T3-L1 adipocytes treated for 24 hours with or without 20 mM sodium salicylate (NaSal), 100 μM PD98059 and 10 ng/ml TNF-α, relative to the activity of ERK1/2 in non treated 3T3-L1 adipocytes. The last line indicates the total amount of ERK1/2 in those cells.

The results, which are shown in FIG. 3, show that TNF-α significantly increases ERK1/2 activation, as shown by the seven fold increase in phosphorylation of the MBP substrate used in the assay. As expected, the MAP kinase inhibitor inhibited ERK1/2 activation, as shown by the fact that MBP phosphorylation was increased only by a factor of less than two in the presence of TNF-α and PD98059. ERK1/2 activation was also inhibited by about two fold by NaSal.

Thus, ERK1/2 activation by TNF-α is also inhibited by NaSal, as is JNK-1, indicating that ERK1/2 may also play a crucial role in TNF-α induced lipolysis in addition to JNK-1.

Example 4

MAP Kinase Inhibitor PD98059 Decreases TNF-α Induced Lipolysis in Mouse and Human Adipocytes This Example demonstrates that inhibition of ERK1/2 by PD98059 decreases TNF-α induced lipolysis. PD98059 specifically reduces ERK activity by blocking its upstream activator MEK-1 (Alessi et al. (1995) J. Biol. Chem. 70: 27489).

3T3-L1 adipocytes prepared as described in Example 1 were incubated for 24 hours with or without 100 μM MAP kinase inhibitor PD98059 and then incubated with or without mTNF-α and with or without 17 μM PGJ2 or 10 μM BRL for 24 hours. The glycerol content in the culture medium was determined as described above.

Figures 2, 4A:
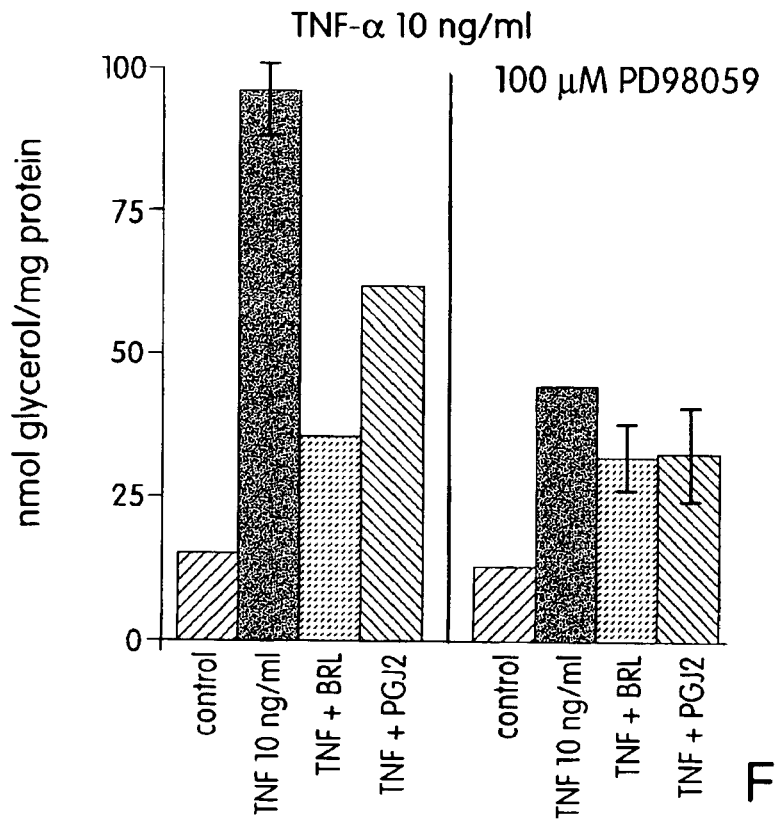

The results, which are presented in FIG. 4, show that PD98059 decreases TNF-α induced lipolysis by a factor of less than 2. In another example, pretreatment for 3 hours (as opposed to 24 hours) resulted in a reduction factor of about 3, i.e., about 76% reduction. Thus, MAP kinase activation is involved in TNF-α induced lipolysis. However, in view of the fact, that the MAP kinase inhibitor used is very efficient (at least about 90% inhibition) in inhibiting MAP kinase activation (as shown in Example 6 and in FIG. 6), and the reduction of TNF-α induced lipolysis is only at most 76%, MAP kinase activation does not seem the be the only factor in TNF-α induced lipolysis. Other signal transduction pathways that may be involved in TNF-α induced lipolysis include cyclic-AMP-dependent protein kinase (PKA) pathway.

Figure 4B:
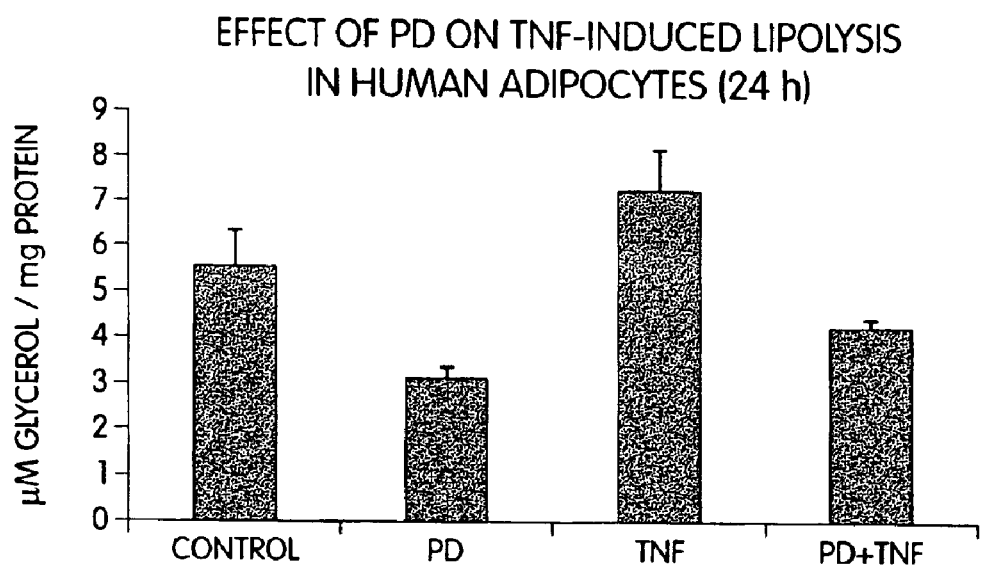
FIG. 4B is a histogram representing the amount of glycerol produced from human adipocytes pretreated or not with PD98059 and treated with or without TNF-α.

Similar results were also obtained using primary cultures of human adipocytes. Primary cultures of human adipocytes, obtained from Zen-Bio were pretreated for 72 hours with PD98059 and then for 24 hours with 100 ng/ml of human TNF-α. The results, which are presented on FIG. 4B show that TNF-α induced lipolysis is also reduced by the MAP kinase inhibitor PD98059 in human cells.

Example 5

Inhibition of p38 Kinase Stimulates TNF-α Induced Lipolysis

This example shows that, contrarily to JNK and ERK1/2 signal pathways, inhibition of the p38 signal pathway stimulates TNF-α induced lipolysis.

3T3-L1 adipocytes prepared as described in Example 1 were preincubated with various amounts (0–50 μM) of the p38 kinase inhibitor SB203580 and then treated with 10 ng/ml TNF-α for 24 hours and the amount of glycerol in the culture medium determined as described above.

Figure 5:
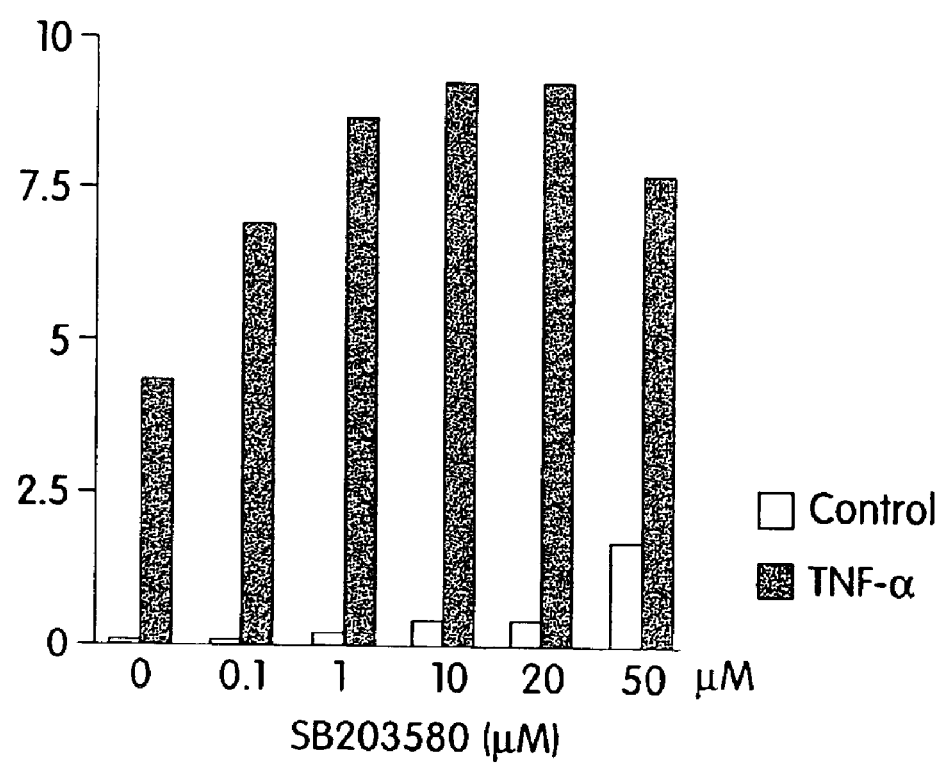
FIG. 5 shows the amount of glycerol produced in 3T3-L1 adipocytes treated for 24 hours with or without TNF-α and increasing amounts of SB203580.

The results, shown in FIG. 5, indicate that the addition of SB203580 to the cells increases the release of glycerol from the adipocytes. Furthermore, the release of glycerol is proportional to the amount of SB203580 added to the cells up to concentrations of 20 μM of SB203580.

Thus, contrary to the JNK and MAP/ERK pathways, whose activity is inhibited in cells in which TNF-α induced lipolysis is reduced, inhibition of the p38 signal pathway stimulates TNF-α induced lipolysis.

Example 6

BRL Decrease in Lipolysis is Mediated by MAP Kinase Activation

As shown above in FIG. 1, BRL is also capable of decreasing TNF-α induced lipolysis. However, this Example shows that the mechanism of action of BRL and salicylic acid in blocking TNF-α induced lipolysis is different.

3T3-L1 adipocytes prepared as described in Example 1 were pretreated for 3 hours with or without 20 mM NaSal or 100 μM PD98059 and then treated for 15 minutes with or without 10 ng/ml mTNF-α and with or without 10 μM BRL. Cell extracts were then prepared and used in ERK 1/2 kinase and JNK-1 kinase assays, as described above.

Figure 6B:
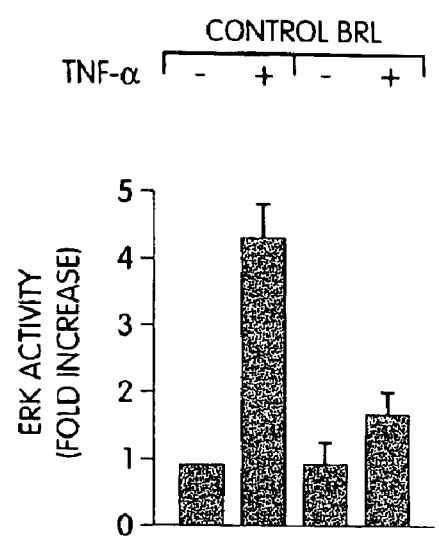
FIG. 6B shows a histogram depicting the activity of ERK in 3T3-L1 cells pretreated with or without BRL for 72 hours, then treated with or without TNF-α in the presence of BRL (or not) for 15 minutes.
Figure 6C:
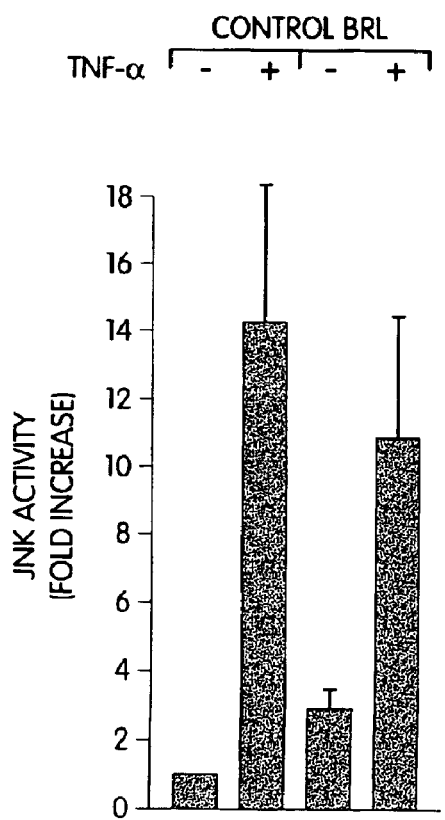
FIG. 6C shows a histogram depicting the activity of JNK in 3T3-L1 cells pretreated with or without BRL for 72 hours, then treated with or without TNF-α in the presence of BRL (or not) for 15 minutes.

The results, shown in FIG. 6A, indicate, that as opposed to NaSal, which decreases JNK-1 kinase activity and to a lesser extent ERK 1/2 kinase activity, BRL does not significantly affect the activity of JNK-1 and ERK 1/2 kinases under the conditions tested. Inhibition of TNF-α induced ERK pathway activation by BRL was, however, observed when the cells were pretreated with BRL. Thus, a 72 hour pretreatment of 3T3-L1 adipocytes with 5 μM BRL prior to TNF-α treatment (10 ng/ml) for 15 minutes in the presence of BRL, resulted in factor of about 2.5 reduction in activation of ERK relative to cells that were not incubated with BRL (see FIG. 6B). Pretreatment did not, however, significantly affect JNK activation (see FIG. 6C). Interestingly, a 24 hour pretreatment failed to prevent activation of ERK. BRL inhibited TNF-α induced lipolysis by greated than 90%.

The 72 hour pretreatment also inhibited basal lipolysis by approximately 30%. However, this reduction was observed in the absence of significant reductions in ERK activity, suggesting that under the conditions of these experiments, BRL can also modulate lipolysis independent of ERK activation.

Example 7

PGJ2 Inhibits TNF-α Induced Activation of JNK-1 and ERK1/2

This example shows that TNF-α induced activation of JNK-1 and ERK1/2 can be inhibited by PGJ2.

3T3-L1 cells were pretreated for 3 days with 17 μM of PGJ2 and then for 15 minutes with 10 ng/ml TNF-α. The amount of phosphorylated (thus activated) JNK-1, ERK1/2, and p38 was determined by Western blot using an antibody specifically recognizing phosphorylated forms of the proteins. As a control, the total amount of JNK-1, ERK1/2 and p38 protein was determined by Western blot using an antibody recognizing the phosphorylated and non phosphorylated forms of the protein. The activity of ERK1/2 and JNK kinases was also determined in a kinase assay using MBP and a portion of c-jun, respectively, as substrate.

Figure 7A:
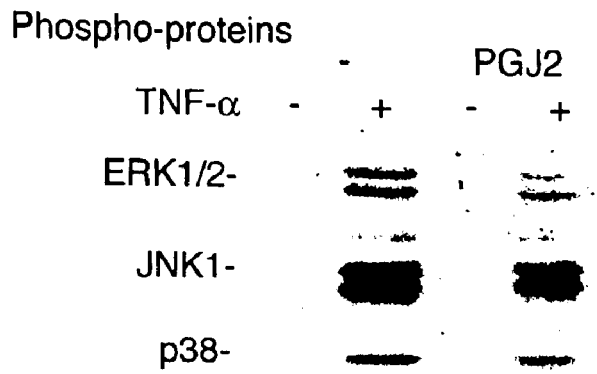
FIG. 7A represents a photograph of a Western blot showing the amount of phosphorylated ERK1/2, JNK-1 and p38 kinases (Panel A) in 3T3-L1 adipocytes pretreated for 3 days with 17 μM PGJ2 or 10 μM BRL and then incubated for 15 minutes with or without 10 ng/ml TNF-α.
Figure 7B:
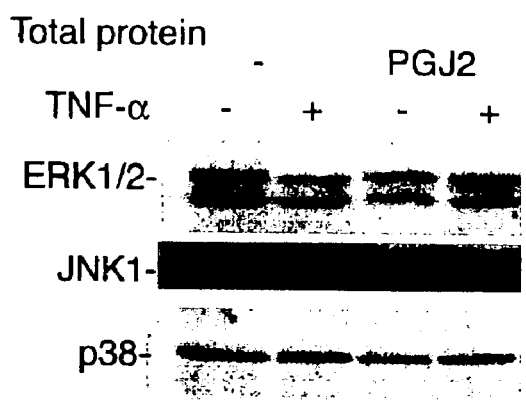
FIG. 7B shows the total amount of ERK1/2, JNK-1 and p38 kinases in 3T3-L1 adipocytes treated as described in FIG. 7A.
Figure 7C:
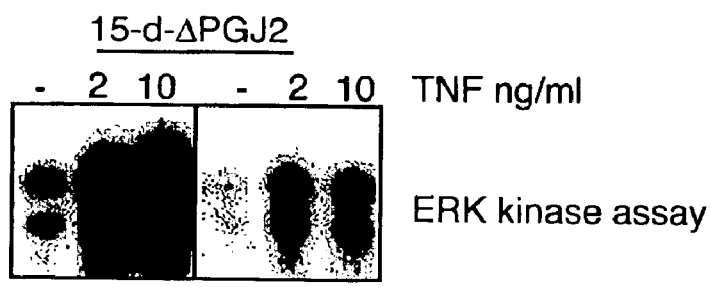
FIG. 7C shows the results of an ERK1/2 kinase assay using proteins extracted from adipocytes treated as described in the legend of FIG. 7A.
Figure 7D:
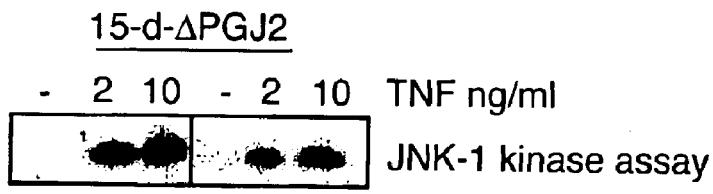
FIG. 7D shows the results of a JNK-1 kinase assay using proteins extracted from adipocytes treated as described in the legend of FIG. 7A.

The results, which are shown in FIG. 7A, indicate that PGJ2 significantly reduces phosphorylation of ERK1/2, JNK-1 and p38. Total protein is shown in FIG. 7 panel B. Furthermore, FIG. 7 panels C and D shows that PGJ2 significantly inhibits the TNF-α induced increase in ERK1/2 and that of JNK-1 kinase activity (to a lesser extent). Thus, PGJ2, which is an agonist of the PPAR-γ receptor may function in a similar manner to NaSal to inhibit TNF-α induced lipolysis, i.e., by modulating MAP kinases, e.g., ERK1/2 and JNK-1. The level of reduction of activation of ERK1/2 by PGJ2 described here is similar to the level of reduction of activation of ERK1/2 by BRL described in Experiment 6 (with a 72 hour pretreatment).

Thus, although previous studies had shown inhibition of ERK signal transduction cascade downstream of ERK kinase, the Examples described here show that PPAR-γ agonists also inhibit ERK activity itself.

Example 8

Method for Inhibiting JNK-1 to Decrease TNF-α Induced Lipolysis

This example demonstrates an experiment that a person of skill in the art can effectuate without undue experimentation to show that inhibition of JNK-1 activity in adipocytes reduces TNF-α induced lipolysis.

For example, 3T3-L1 fibroblasts can be transfected with a construct encoding an antisense nucleic acid, inhibiting JNK-1 synthesis and the transfected fibroblasts can then be induced to differentiate into adipocytes. One differentiated, the transfected or anti adipocytes, as well as non transfected or control transfected adipocytes are treated with TNF-α and the amount of glycerol or FFA is determined as described above. One can also perform a control experiment to confirm that the level of JNK-1 kinase is lower in the adipocytes expressing JNK-1 antisens nucleic acid than in control adipocytes. A lower level of lipolysis in adipocytes expressing JNK-1 antisens indicates that inhibition of JNK-1 activity in adipocytes reduces TNF-α induced lipolysis. Instead of transfecting 3T3-L1 fibroblasts, one can also contact 3T3-L1 adipocytes with JNK-1 antisens oligonucleotides.

Example 9

BRL and PD98059 Reduce TNF-α Decrease in Perilipin A and HSL in Adipocytes

This example shows that the decrease in perilipin A and hormone-sensitive-lipase (HSL) induced by TNF-α in cells can be reduced by BRL and by PD98059.

3T3-L1 adipocytes were treated with TNF-α at 10 ng/ml, TNF-α plus BRL (10 μM), or BRL alone for 24 hours, following which cell lysates were collected and analyzed by Western blotting using antibodies against HSL and perilipin A proteins. Perilipin antibodies were generated by immunization of rabbits with a peptide identical to amino acids 9–23 of the rat perilipin protein (Greenberg et al. (1993) PNAS 90:12035). Antibodies to HSL were prepared by injecting a peptide based upon the rat HSL sequence (GeneBank) (KDLSFKGNSPEPSDSPEMC; SEQ ID NO: 1) into rabbits. Antibodies were subsequently affinity purified and used for Western blotting at a dilution of 1:1500. Western blotting was performed as follows: adipocytes are briefly rinsed with 1 ml of phosphate saline buffer (PBS, pH 7.4). Proteins were extracted by adding 200 µl of lysis buffer containing 50 mM Hepes, pH 7.4, 100 mM Nacl, 2 mM EDTA, 5% SDS, 0.1 mM Na3V) 4 , 50 mM NaF, 1 mM benzamidine, 100 µM AEBSF, adn 10 µg/ml aprotinin. Equivalent amounts of protein were separated by 10% SDS-PAGE, electrophoretically transferred to nitrocellulose membranes, incubated with primary antibody and subsequentely with donkey anti-rabbit IgG conducaged with horseradish peroxidase. Proteins were detected with enhanced chemiluminescence (ECL) system (Amersham).

Figure 8A:
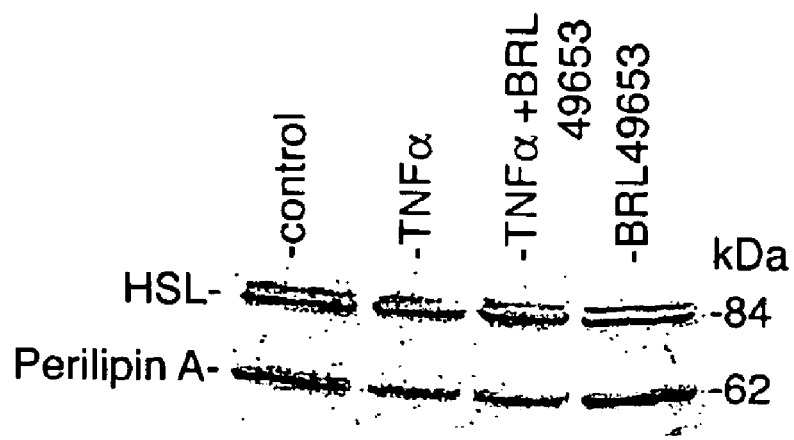
FIG. 8A represents a photograph of a Western blot showing the amount of HSL and perilipin A proteins in 3T3-L1 adipocytes treated for 24 hours with or without TNF-α and BRL.

The results, which are shown in FIG. 8A, show that TNF-α markedly decreased the expression of perilipin A protein and slightly decreased HSL protein expression as compared with untreated controls. In another example, pretreatment of the cells for 72 hours with BRL also blocked downregulation of perilipin A by TNF-α. BRL partially antagonized the actions of TNF-α on expression of perilipin A and HSL proteins, indicating that BRL modulates adipocyte lipolysis at least in part by altering adipocyte protein expression. Nuclear run-on assays indicate that this effect of BRL on perilipin expression occurs at the level of transcription.

Figure 8B:
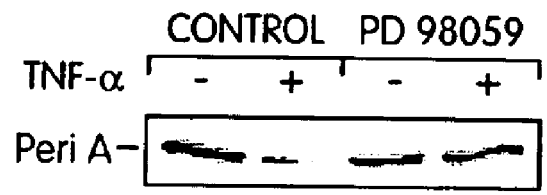
FIG. 8B shows a photograph of a Western blot showing the amount of perilipin A protein in 3T3-L1 adipocytes treated for 24 hours with or without TNF-α and PD98059.

In another example, 3T3-L1 cells were preincubated with PD98059 prior to the addition of TNF-α as described above. A similar reduction in TNF-α induced downregulation of perilipin A was observed (FIG. 8B). These results further demonstrate the involvement of ERK in perilipin A downregulation, and more generally, in TNF-α induced lipolysis.

Example 10

Overexpression of Perilipin A Blocks TNF-α Induced Lipolysis

This example demonstrates that overexpression of perilipin A in adipocytes protects these cells against TNF-α induced lipolysis.

Figure 9:
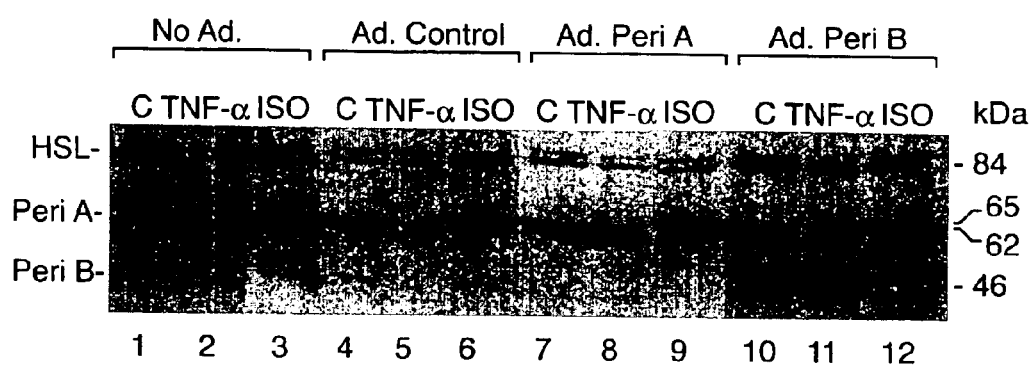
FIG. 9 represents a photograph of a Western blot showing the level of HSL, perilipin A and perilipin B proteins in control 3T3-L1 adipocytes (No Ad.), 3T3-L1 adipocytes infected with a control adenoviral vector (Ad. Control), infected with an adenoviral vector encoding perilipin A (Ad. Peri A), or infected with an adenoviral vector encoding perilipin B (Ad. Peri B) and further treated with or without TNF-α and isoproterenol.
Figure 10A:
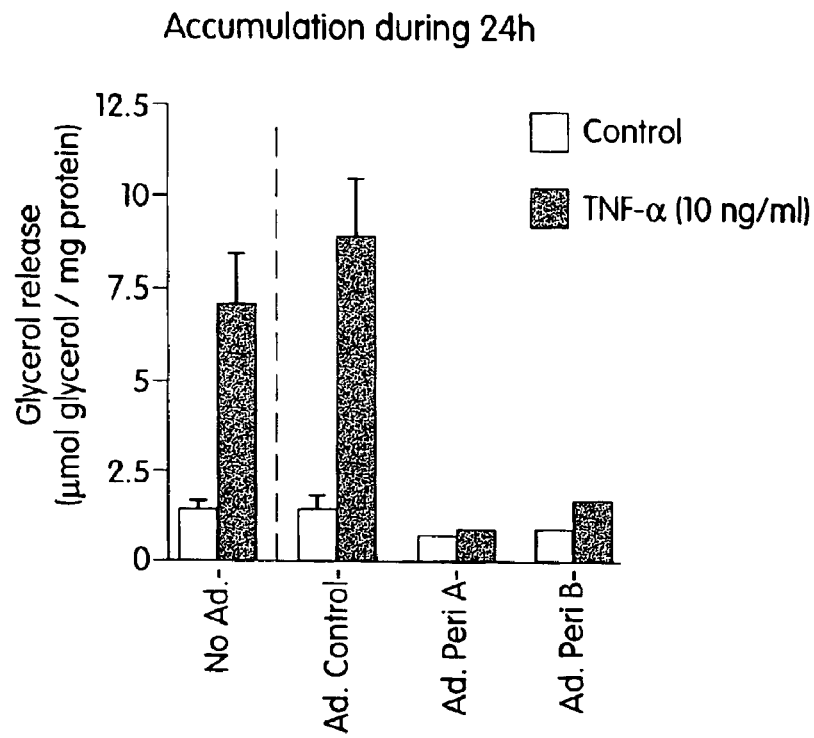
FIG. 10A shows the amount of glycerol that accumulated during a 24 hour incubation of 3T3-L1 adipocytes with or without TNF-α, after infection of the cells with or without an adenoviral vector encoding or not perilipin A (Ad. Peri A) and perilipin B (Ad. Peri B).
Figure 10B:
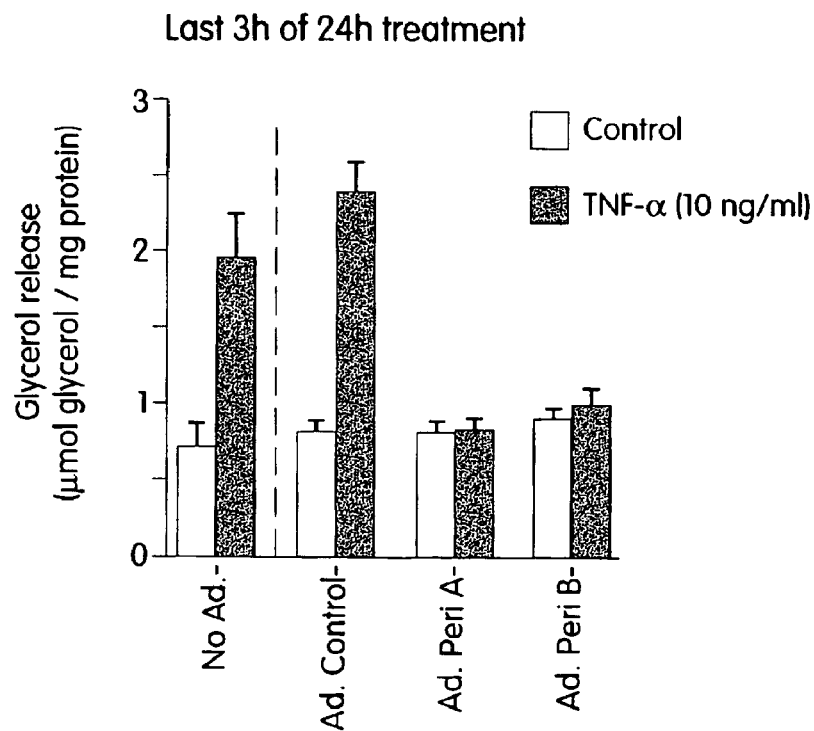
FIG. 10B shows the amount of glycerol that accumulated for the last 3 hours of a 24 hour incubation of 3T3-L1 adipocytes with or without TNF-α, after infection of the cells with or without an adenoviral vector encoding or not perilipin A (Ad. Peri A) and perilipin B (Ad. Peri B).

3T3 L1 were incubated for 24 hours with or without TNF-α at 10 ng/ml and simulatenously incubated with or without an adenoviral vector expressing perilipin A or perilipin B. The adenoviral vector was prepared as follows. After the 24 hours incubation, the glycerol level in the culture medium was determined as set forth above. Expression of perilipin A and B was visualized by performing a Westen blot analysis. As shown in FIG. 9, significant levels of perilipin A and B were expressed in the cells following infection with the perilipin A and perilipin B adenoviral vectors. Furthermore, as shown in FIG. 10A, incubation of the cells with an adenoviral vector expressing perilipin A or B, essentially inhibited completely lypolysis induced by TNF-α, whereas the adenoviral vector alone had no effect on TNF-α induced lipolysis. As shown in FIG. 10B, TNF-α induced lipolysis was still inhibited during the last 3 hours of the 24 hour treatment. On the contrary, perilipin A or B overexpression did not significantly block isoprenol (10 µM) induced lipolysis. As shown in FIG. 8, isoprenol did not decrease perilipin expression either, indicating that isoprenol induces lipolysis through a mechanism that is different from that of TNF-α.

Example 11

Direct Correlation Between Circulating TNF-α Levels and Percentage Body Fat

To demonstrate a link between TNF-α levels and obesity, the amount of serum level of TNF-α (circulating TNF-α) was determined in individuals having different percentages of body fat. The level of circulating TNF-α, IL-6 and leptin was determined by ELISA.

The results, which are represented graphically in FIG. 11, indicate that there is a direct correlation between the percentage of body fat in an individual and the level of circulating TNF-α. A direct correlation between circulating IL-6 and percentage body fat was also observed, as well as a direct correlation between circulating leptin levels and percentage body fat.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A drug screening method for identifying a compound which reduces TNF-α induced lipolysis comprising
   i) isolating a compound which is an inhibitor of ERK1, ERK2, or JNK, comprising contacting a candidate compound or a library of candidate compounds with one of ERK1, ERK2, or JNK, and assaying for a change in the expression or activity of ERK1, ERK2, or JNK, wherein a compound that decreases said expression or activity thereby indicates that the compound is an inhibitor of ERK1, ERK2, or JNK, and
   ii) contacting an adipocyte with the inhibitor of step (i) and TNF-α and determining the level of lipolysis, wherein a lower level of lipolysis in the presence of the inhibitor of step (i) relative to the level of lipolysis in the absence of the inhibitor of step (i) and wherein a similar level of lipolysis in the presence of the inhibitor relative to the absence of the compound when tested in the absence of TNF-α indicates that the compound reduces TNF-α induced lipolysis, to thereby identify a compound which reduces TNF-α induced lipolysis.

2. A drug screening method for identifying a compound which reduces TNF-α induced lipolysis comprising
   i) isolating a compound which is an inhibitor of ERK1 or ERK2, comprising contacting a candidate compound or a library of candidate compounds with one of ERK1 or ERK2, and assaying for a change in the expression or activity of ERK1 or ERK2, wherein a compound that decreases said expression or activity thereby indicates that the compound is an inhibitor of ERK1 or ERK2, and
   ii) contacting an adipocyte with the inhibitor of step (i) and TNF-α and determining the level of lipolysis, wherein a lower level of lipolysis in the presence of the inhibitor of step (i) relative to the level of lipolysis in the absence of the inhibitor of step (i) and wherein a similar level of lipolysis in the presence of the inhibitor relative to the absence of the compound when tested in the absence of TNF-α indicates that the compound reduces TNF-α induced lipolysis, to thereby identify a compound which reduces TNF-α induced lipolysis.

3. A drug screening method for identifying a compound which reduces TNF-α induced lipolysis comprising
   i) isolating a compound which is an inhibitor of JNK, comprising contacting a candidate compound or a library of candidate compounds with JNK, and assaying for a change in the expression or activity of JNK, wherein a compound that decreases said expression or activity thereby indicates that the compound is an inhibitor of JNK, and
   ii) contacting an adipocyte with the inhibitor of step (i) and TNF-α and determining the level of lipolysis, wherein a lower level of lipolysis in the presence of the inhibitor of step (i) relative to the level of lipolysis in the absence of the inhibitor of step (i) and wherein a similar level of lipolysis in the presence of the inhibitor relative to the absence of the compound when tested in the absence of TNF-α indicates that the compound reduces TNF-α induced lipolysis, to thereby identify a compound which reduces TNF-α induced lipolysis.

4. The method of claim 1, 2, or 3, wherein said level of TNF-α induced lipolysis is measured by levels of free fatty acid or glycerol in the cell medium.

* * * * *

UNITED STATES PATENT AND TRADEMARK OFFICE
CERTIFICATE OF CORRECTION

PATENT NO.     : 6,897,019 B1
DATED          : May 24, 2005
INVENTOR(S)    : Andrew S. Greenberg It is certified that error appears in the above-identified patent and that said Letters Patent is hereby corrected as shown below:

<u>Title page,</u>
Item [76], Inventor, replace "Andrew S. Greenberg, 711 Washingon St., Boston, MA (US) 02111" with -- Andrew S. Greenberg, 110 Rachel Road, Newton, MA 02459 --.
Insert Item -- [73] Assignee: Trustees of Tufts College
                               Tufts University (Medford, MA) --.

Signed and Sealed this

Twenty-seventh Day of September, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 19
<212> TYPE: PRT
<213> ORGANISM: Rattus sp.

<400> SEQUENCE: 1

Lys Asp Leu Ser Phe Lys Gly Asn Ser Pro Glu Pro Ser Asp Ser Pro
 1               5                  10                  15

Glu Met Cys